United States Patent
Conway et al.

(10) Patent No.: US 10,202,568 B2
(45) Date of Patent: Feb. 12, 2019

(54) AUTOMATED CELL CULTURE SYSTEM AND METHOD

(71) Applicant: INVIVOSCIENCES INC., Madison, WI (US)

(72) Inventors: Michael Conway, Madison, WI (US); Michael Gerger, Madison, WI (US); Tetsuro Wakatsuki, Madison, WI (US)

(73) Assignee: INVIVOSCIENCES INC., McFarland, WI (US)

( * ) Notice: Subject to any disclaimer, the term of this patent is extended or adjusted under 35 U.S.C. 154(b) by 0 days.

(21) Appl. No.: 14/910,641

(22) PCT Filed: Aug. 12, 2014

(86) PCT No.: PCT/US2014/050704
§ 371 (c)(1),
(2) Date: Feb. 5, 2016

(87) PCT Pub. No.: WO2015/023658
PCT Pub. Date: Feb. 19, 2015

(65) Prior Publication Data
US 2016/0177244 A1  Jun. 23, 2016

Related U.S. Application Data

(60) Provisional application No. 61/864,993, filed on Aug. 12, 2013.

(51) Int. Cl.
  C12M 1/32 (2006.01)
  C12M 1/34 (2006.01)
  C12M 1/36 (2006.01)
  C12M 1/26 (2006.01)

(52) U.S. Cl.
  CPC ............ *C12M 23/12* (2013.01); *C12M 33/06* (2013.01); *C12M 33/07* (2013.01); *C12M 41/12* (2013.01); *C12M 41/36* (2013.01); *C12M 41/48* (2013.01)

(58) Field of Classification Search
None
See application file for complete search history.

(56) References Cited

U.S. PATENT DOCUMENTS

| | | |
|---|---|---|
| 5,424,209 A | 6/1995 | Kearney |
| 5,612,188 A | 3/1997 | Shuler et al. |
| 7,101,511 B2 * | 9/2006 | Toi et al. |
| 7,787,681 B2 | 8/2010 | Zhang et al. |
| 7,874,324 B2 | 1/2011 | Kubacki |
| 7,976,792 B2 | 7/2011 | Shivji |
| 8,311,626 B2 | 11/2012 | Hlavka et al. |
| 8,414,765 B2 | 4/2013 | Uber et al. |
| 2004/0094575 A1 | 5/2004 | Toi et al. |
| 2009/0029462 A1 | 1/2009 | Beardsley et al. |
| 2009/0075385 A1 | 3/2009 | Fournier et al. |
| 2009/0304257 A1 | 12/2009 | Ohjo et al. |
| 2012/0009559 A1 | 1/2012 | Felder et al. |
| 2012/0034596 A1 | 2/2012 | Seidl et al. |
| 2013/0189723 A1 | 7/2013 | Felder et al. |

FOREIGN PATENT DOCUMENTS

| | | |
|---|---|---|
| JP | 2008-526188 | 7/2008 |
| JP | 2010-521148 | 6/2010 |
| JP | 2010-532173 | 10/2010 |
| JP | 2012-520058 | 9/2012 |
| JP | 2013-102723 | 5/2013 |
| WO | 2006/090750 | 7/2008 |
| WO | 2008107695 | 9/2008 |
| WO | 2009/130318 | 10/2009 |

OTHER PUBLICATIONS

Thomas et al., Biotechnology and Bioengineering, 2009, vol. 102, Issue 6, p. 1636-1644.*
Hamilton Robotics Application Solution, Jun. 2011, 3 pages of PDF.*
Animal Stem Cells, Amita Sarkar, Discovery Publishing House, 2009, pp. 271 and 280 Only.*
Hamilton Robotics Application Solution, 2011, 3 pages of PDF.*
J.G. Finneran.com, 8 and 12 channel reservoir trough plates, Jul. 2012, 2 pages of PDF.*
Asnes, C.F., et al., Reconstitution of the Frank-Starling mechanism in engineered heart tissues. Biophys J, 2006. 91(5): p. 1800-1810.
Chen, G., D. R. Gulbranson, et al. (2011). "Chemically defined conditions for human iPSC derivation and culture." Nature methods 8(5): 424-429.
Ebert, A. D., P. Liang, et al. (2012). "Induced Pluripotent Stem Cells as a Disease Modeling and Drug Screening Platform." Journal of Cardiovascular Pharmacology 60(4): 408-416.
European Extended Search Report for Application No. 14835984.7 dated Feb. 17, 2017 (7 pages).
Ferreira, L. M. R. and M. A. Mostajo-Radji (2013). "How induced pluripotent stem cells are redefining personalized medicine." Gene 520(1 ): 1-6.

(Continued)

*Primary Examiner* — Kade Ariani
(74) *Attorney, Agent, or Firm* — Michael Best & Friedrich LLP

(57) ABSTRACT

An automated method for culturing stem cells using a robotic liquid handling system including a translatable bed and a movable multichannel pipette. The method includes the steps of: locating a first multi-well cell culture plate and a multi-trough plate on the bed; placing a suspension of stem cells in at least one trough of the multi-trough plate; using the multi-channel pipette, transferring a portion of the suspension of stem cells to each well of the first multi-well cell culture plate such that at least two of the wells of the first multi-well cell culture plate have different densities of stem cells; selecting a well of the first multi-well cell culture plate having a desired stem cell density; locating a second multi-well cell culture plate; and using the multi-channel pipette, transferring the cells of the selected well to a plurality of wells of the second multi-well cell culture plate.

19 Claims, 36 Drawing Sheets

(56) References Cited

OTHER PUBLICATIONS

Haraguchi, Y., K. Matsuura, et al., "Simple suspension culture system of human iPS cells maintaining their pluripatency for cardiac cell sheet engineering." Journal of Tissue Engineering and Regenerative Medicine, 2015, 9: 1363-1375.

Hazeltine, L.B., C. S. Simmons, et al. (2012). "Effects of substrate mechanics on contractility of cardiomyocytes generated from human pluripotent stem cells." International journal of cell biology 2012: 508294.

Jung, S., K. M. Panchalingam, et al. (2012). "Large-scale production of human mesenchymal stem cells for clinical applications." Biotechnology and applied biochemistry 59(2): 106-120.

Kehoe, D. E., D. Jing, et al. (2010). "Scalable stirred-suspension bioreactor culture of human pluripotent stem cells." Tissue engineering. Part A 16(2): 405-421.

Lian, X., C. Hsiao, et al. (2012). "Robust cardiomyocyte differentiation from human pluripotent stem cells via temporal modulation of canonical Wnt signaling." Proceedings of the National Academy of Sciences of the United States of America 109(27): E1848-1857.

Lian, X., J. Zhang, et al. (2013). "Directed cardiomyocyte differentiation from human pluripotent stem cells by modulating Wnt/beta-catenin signaling under fully defined conditions." Nature protocols 8(1): 162-175.

Lotz, S., S. Goderie, et al. (2013). "Sustained levels of FGF2 maintain undifferentiated stem cell cultures with biweekly feeding." PLoS One 8(2): e56289.

Ludwig, T.E., et al., Feeder-independent culture of human embryonic stem cells. Nat Meth, 2006. 3(8): p. 637-646.

Marquez, J.P., et al., High-Throughput Measurements of Hydrogel Tissue Construct Mechanics. Tissue Eng Part C Methods, 2009, pp. 181-190.

Muller, F. J., B. M. Schuldt, et al. (2011). "A bioinformatic assay for pluripotency in human cells." Nature methods 8(4): 315-317.

Outten, J. T., X. Cheng, et al. (2011). "A high-throughput multiplexed screening assay for optimizing serum-free differentiation protocols of human embryonic stem cells." Stem Cell Research 6(2): 129-142.

Syed, B. A. and J. B. Evans (2013). "Stem cell therapy market." Nature reviews. Drug discovery 12(3): 185-186.

Takahashi, K. and S. Yamanaka (2006). "Induction of pluripotent stem cells from mouse embryonic and adult fibroblast cultures by defined factors." Cell 126(4): 663-676.

Walker, J. (2010). "Disease in a dish: a new approach to drug discovery." Regenerative medicine 5(4): 505-507.

Wetterstrand, K. A. "DNA Sequencing Costs: Data from the NHGRI Genome Sequencing Program (GSP) Available at: www.genome.gov/sequencingcosts." (Last Updated May 24, 2016).

International Preliminary Report on Patentability and Written Opinion for application No. PCT/US2014/050704 dated Feb. 16, 2016 (9 pages).

Japanese Patent Office Action for Application No. 2016-534790 dated Jun. 26, 2018 (13 pages, English translation included).

Funakoshi general Catalogue 2005-2006 Devices Edition, Funakoshi Co., Ltd., pp. 422-424.

\* cited by examiner

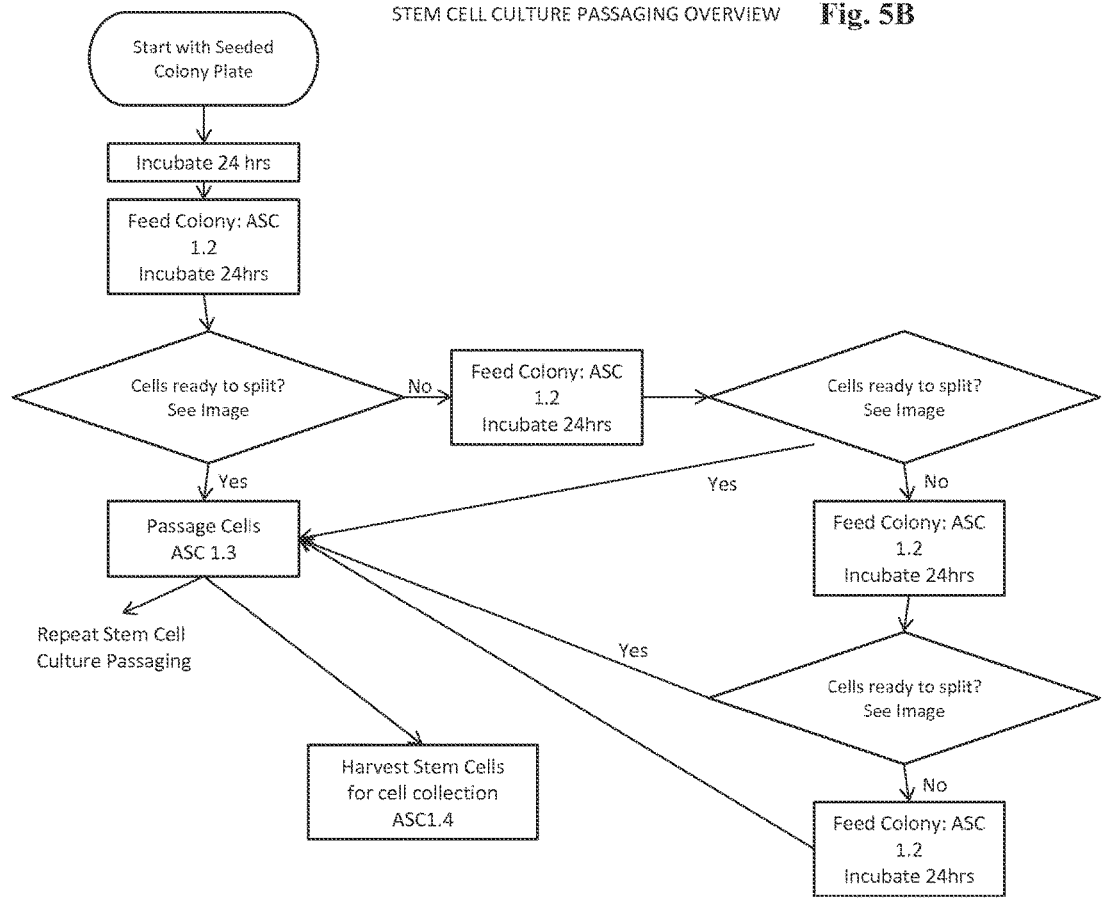

Matrigel Aliquot/DMEM:F12 Dispense
IVS Program: IVS Matrigel Aliquot 2 Plate

Matrigel Aliquot/DMEM:F12 Dispense
IVS Program: IVS Matrigel Aliquot 1 Plate

Density Gradient Stem Cell Seed
IVS Program: *IVS Density Gradient*

Stem Cell Harvest Layout

Stem Cell Passaging Split Layout

Stem Cell Passaging Split Layout
IVS Program: *IVS Stem Cell Colony Split*

Stem Cell Passaging Split Layout

Stem Cell Passaging Split Step1

Stem Cell Colony Split
'StemColonyPassage 2columns to 2plates'

Collecting maximum cells out of 96 Well Plate

Cell Collection from 96 well plate

FIG. 32

Tilt 96 Well Plate

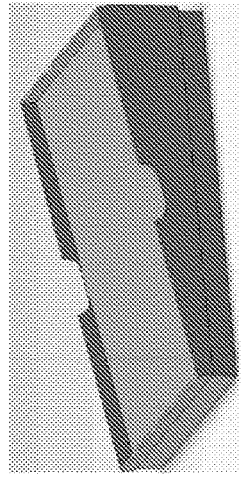

Having a tilt plate allows for tips
To reach the corner of the wells
In a 96 well plate This allows for more liquid removal
Producing a higher yield for cell
Collection Media Surface Tension:
Attracted to corners
Remove more media
When tips are closer to edge Need tips as close to edge as possible
for maximal liquid removal

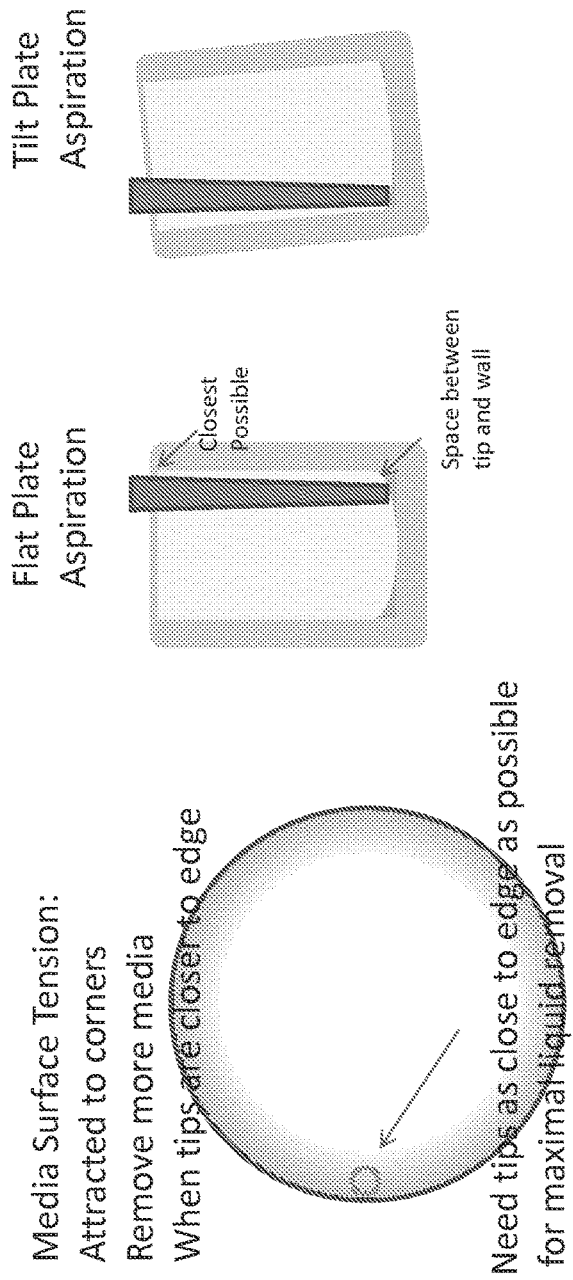

Flat Plate Aspiration

Closest Possible

Space between tip and wall

Tilt Plate Aspiration

Feeding Single Cells

A fully confluent plate with differentiating stem cells are very fragile to fluid flow puncturing the tissue layer Our feed was modified to position the Tips to dispense along the edge of the well Tips lowered   Tips positioned   Dispense Liquid flows slowly down
Edge to minimize droplets
Or a stream from puncturing
Tissue layer

AUTOMATED CELL CULTURE SYSTEM AND METHOD

CROSS-REFERENCE TO RELATED APPLICATIONS

This is a U.S. national stage entry of International Patent Application No. PCT/US2014/050704, filed on Aug. 12, 2014, which claims priority to U.S. Provisional Patent Application No. 61/864,993, filed on Aug. 12, 2013, the entire contents of all of which are incorporated herein fully by reference.

GOVERNMENT SUPPORT STATEMENT

This invention was made with government support under R44 GM087784 and R01 HL109505 awarded by the National Institutes of Health. The government has certain rights in the invention.

INTRODUCTION

The potential to reprogram human fibroblasts into pluripotent cells has opened up an opportunity of personalized medicine using unlimited numbers of patient-specific pluripotent stem cells. Indeed, developing the "Disease in a Dish" concept is becoming closer to reality.

The advantages of induced pluripotent stem cells (iPSCs) and other types of pluripotent stem cells include their multipotency and the fact that they can be established from individuals, allowing the creation of pluripotent stem cells from any donor with any genetic background. Pluripotent stem cells can differentiate into any cell type, which makes them an attractive resource in fields such as regenerative medicine, drug screening, and in vitro toxicology.

The most important prerequisite for such applications is a stable supply and uniform quality of the iPSCs. Variation in quality largely results from differences in handling skills between operators in laboratories.

Cell cultivation is an essential process in stem cell research and in high throughput, high content cell-based screening. Cell culture is a complex process consisting of multiple tasks, including cell seeding, growing, harvesting, counting, and passaging. Those applications require very time-consuming processes for formulation development, cell isolation, and evaluation in order to ensure reproducibility. Processes for establishing stem cell lines may need to run for weeks or months under the demands of maintaining sterility and managing all relevant data information.

Conventional culture methods and systems are labor-intensive and suffer from drawbacks such as contamination and varying levels of culturing success due to human error and lack of continual performance evaluation. Conventional culture systems require that most of the initial steps in the preparation of cells for seeding (i.e. tissue digestion, cell selection) is performed manually which is time consuming, unreliable in terms of the quality of the tissue produced, and prone to culture contamination problems. The systems are incapable of supporting the automated preparation of tissue engineered implants from primary or precursor cells due to inherent design limitations that restrict the cell and tissue culture process, the inability to adequately monitor and modify the environment to support tissue development, and the absence of techniques to enable the implementation of effective quality control measures.

SUMMARY OF THE INVENTION

In one aspect, an automated method for culturing stem cells using a robotic liquid handling system including a translatable bed and a movable multi-channel pipette. The method includes the steps of: locating a first multi-well cell culture plate and a multi-trough plate on the bed; placing a suspension of stem cells in at least one trough of the multi-trough plate; using the multi-channel pipette, transferring a portion of the suspension of stem cells to each well of the first multi-well cell culture plate such that at least two of the wells of the first multi-well cell culture plate have different densities of stem cells; selecting a well of the first multi-well cell culture plate having a desired density of stem cells; locating a second multi-well cell culture plate on the bed; and using the multi-channel pipette, transferring the cells of the selected well to a plurality of wells of the second multi-well cell culture plate.

In another aspect, an automated system for culturing stem cells. The system includes a robotic liquid handling system and a controller in communication with the robotic liquid handling system. The robotic liquid handling system includes a translatable bed and a movable multi-channel pipette, the bed having a first multi-well cell culture plate, a second multi-well cell culture plate, and a multi-trough plate located thereon. The controller is configured to place a suspension of stem cells in at least one trough of the multi-trough plate; using the multi-channel pipette, transfer a portion of the suspension of stem cells to each well of the first multi-well cell culture plate such that at least two of the wells of the first multi-well cell culture plate have different densities of stem cells; obtain user input to select a well of the first multi-well cell culture plate having a desired density of stem cells; and using the multi-channel pipette, transfer the cells of the selected well to a plurality of wells of the second multi-well cell culture plate.

BRIEF DESCRIPTIONS OF THE DRAWINGS

Embodiments described herein may be better understood and appreciated by reference to the detailed description presented herein in conjunction with the accompanying drawings, of which:

FIG. 1a shows the multi-potential of stem cell differentiation from patient cells, and FIG. 1b shows a diagram of iterative optimization or high-throughput (HTP) screening of culture conditions in iPSC culture optimization;

FIGS. 5A-5F are flow diagrams illustrating a system of the present invention for culturing cells.

FIGS. 29-33 show diagrams of features of the disclosed methods and systems.

DETAILED DESCRIPTION

Figure 1:
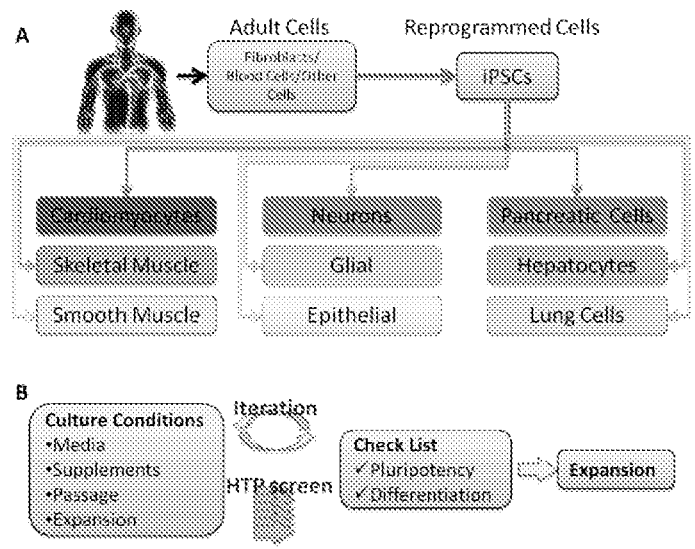
FIGS. 1a and 1b are schematic diagrams illustrating pluripotent stem cell differentiation and scale up cell production.

Before any embodiments are explained in detail herein, however, it is to be understood that the embodiments are not limited in application to the details of construction and the arrangement of components of processes set forth in the following description, illustrated in the following drawings or exemplified by the Examples. Such description, drawings, and Examples are not intended to limit the scope of the embodiments of the processes described herein as set forth in the appended claims. Other embodiments can be practiced or carried out in various other ways.

Further, no admission is made that any reference, including any patent or patent document, cited in this specification constitutes prior art. In particular, it will be understood that, unless otherwise stated, reference to any document herein does not constitute an admission that any of these documents form part of the common general knowledge in the prior art in the United States or in any other country. Any discussion of the references states what their authors assert, and the applicant reserves the right to challenge the accuracy and pertinence of any of the documents cited herein.

Throughout this disclosure, various aspects of the methods and systems described herein may be presented in a range format. It should be understood that the description in range format is merely for convenience and brevity, and should not be construed as an inflexible limitation on the scope of the processes described herein. Accordingly, as will be understood by one skilled in the art, for any and all purposes, particularly in terms of providing a written description, all ranges disclosed herein also encompass any and all possible subranges and combinations of subranges thereof, as well as all integral and fractional numerical values within that range. As only one example, a range of 20% to 40% can be broken down into ranges of 20% to 32.5% and 32.5% to 40%, 20% to 27.5% and 27.5% to 40%, etc. Any listed range is also easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. Further, as will also be understood by one skilled in the art, all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio. Further, the phrases "ranging/ranges between" a first indicate number and a second indicate number and "ranging/ranges from" a first indicate number "to" a second indicate number are used herein interchangeably. The foregoing are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method. Unless specified or limited otherwise, the terms such as "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

In various embodiments, the disclosed methods may be implemented on one or more computer systems. Each computer system may be in wired or wireless communication with one another through a combination of local and global networks including the Internet. Each computer system may include one or more input device, output device, storage medium, and processor/microprocessor. Possible input devices include a keyboard, a computer mouse, a touch pad, a touch screen, a digital tablet, a microphone, a track ball, and the like. Output devices include a cathode-ray tube (CRT) computer monitor, a liquid-crystal display (LCD) or LED computer monitor, touch screen, speaker, and the like. Storage media include various types of local or remote memory devices such as a hard disk, RAM, flash memory, and other magnetic, optical, physical, or electronic memory devices. The processor may be any typical computer processor for performing calculations and directing other functions for performing input, output, calculation, and display of data in accordance with the disclosed methods. In various embodiments, implementation of the disclosed methods includes generating sets of instructions and data (e.g. including image data and numerical data) that are stored on one or more of the storage media and operated on by a controller.

In some embodiments, implementation of the disclosed methods may include generating one or more web pages for facilitating input, output, control, analysis, and other functions. In other embodiments, the methods may be implemented as a locally-controlled program on a local computer system which may or may not be accessible to other computer systems. In still other embodiments, implementation of the methods may include generating and/or operating modules which provide access to portable devices such as laptops, tablet computers, digitizers, digital tablets, smart phones, and other devices.

It should also be noted that a plurality of hardware and software based devices, as well as a plurality of different structural components may be used to implement the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification can include one or more processors, one or more memory modules including non-transitory computer-readable medium, one or more input/output interfaces, and various connections (e.g., a system bus) connecting the components.

Figure 2:
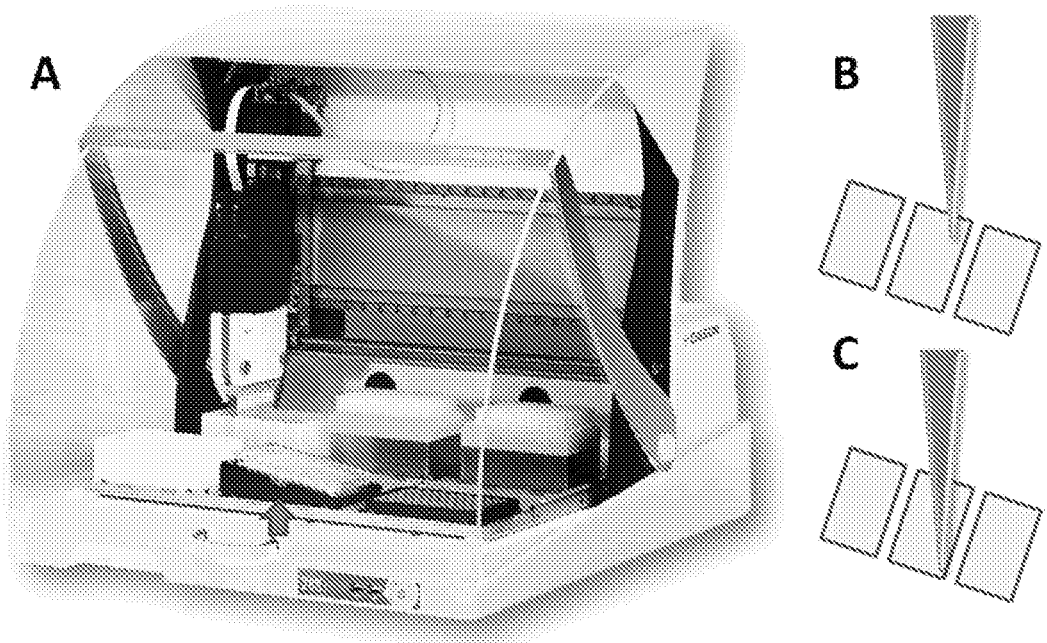
FIG. 2a is a perspective view of an automated robotic liquid handling system with an eight-channel pipette head.
FIGS. 2b, 2c show guidance of a pipette tip into a well of a tilted multi-well plate.

An automated cell culture method and system has been developed which handles fragile pluripotent stem cells to identify an optimal culture condition and to scale up production of those cells while maintaining pluripotency of the stem cells (FIG. 1a). In various embodiments the method and system utilize an automated, multi-channel robotic liquid handling (e.g. a unit such as the PipetmaX™) system from Gilson, Inc. or equivalent systems from other suppliers, including systems from Agilent, Tecan, Hamilton, or Biotek, to perform stem cell culture (FIG. 2a). One aspect of the disclosed system and method includes an application software program (app) to run programmed protocols on the robotic liquid handling system to automate culture of stem cells such as iPSCs; while many of the examples disclosed herein specifically refer to iPSCs, in various embodiments the disclosed methods and systems are also applicable to other pluripotent stem cells including pluripotent human embryonic-derived stem cells. The software program may run on an external device (e.g. a tablet computer) which is in communication with a controller built into the robotic liquid handling system; the software program in some embodiments will coordinate control of the robotic liquid handling system and, when present, the external robotic system as well, to implement the disclosed methods and systems. The software program may be programmed to alert users (e.g. using sound, light, vibration, email alerts, text alerts, etc.) when intervention is needed, either due to a fault/error (e.g. no pipette tips available) or due to a procedure being completed. In general no intervention is needed during running of the procedures such as feeding, passing, or harvesting of stem cells. The disclosed procedures therefore automate some or all of the steps involved in maintaining pluripotent stem cells and differentiating the stem cells into various cell and tissue types. In addition to freeing up laboratory personnel, the disclosed automated methods and systems enable these techniques to be carried out by minimally-trained personnel in a reliable and reproducible manner.

An aspect of the system and method is the use of multi-well (e.g. 24-, 48-, or 96-well) plates to perform screening to identify optimal conditions for cell culture and for scale-up of cell production (FIG. 1b). Use of a multi-well plate format, which is facilitated by the use of a robotic liquid handling system, minimizes the cost (including costs resulting from time and materials) of establishing new cell culture protocols specific to different pluripotent stem cell lines. A reliable, automated stem cell handling system frees scientists from routine cell culture so that they can devote their effort in translating their laboratory discovery to clinical applications as quickly as possible. Use of the disclosed an automated stem cell handling system and method for maintaining the pluripotency of various stem cell lines ensures reproducibility of stem cell culture by having a standardized interaction with the system, e.g. through users clicking buttons in a computer application using a robotic system and use of standardized materials and reagents.

Features of the disclosed method and system include: 1) use of multi-well (e.g. 96 well) plates in both screening culture conditions and scale-up cell production; 2) use of a robotic liquid handling system having a capability to move pipette positions with high levels (e.g. submicron) of precision to dispense and collect cell culture medium; 3) use of heated/tilted racks for ~99% recovery of cells (FIGS. 2a, 2b, 2c); 4) elimination of a need for centrifugation steps for passaging cells; and 5) achievement of a rapid stem cell expansion rate (e.g. 144-fold in one week).

Figure 3:
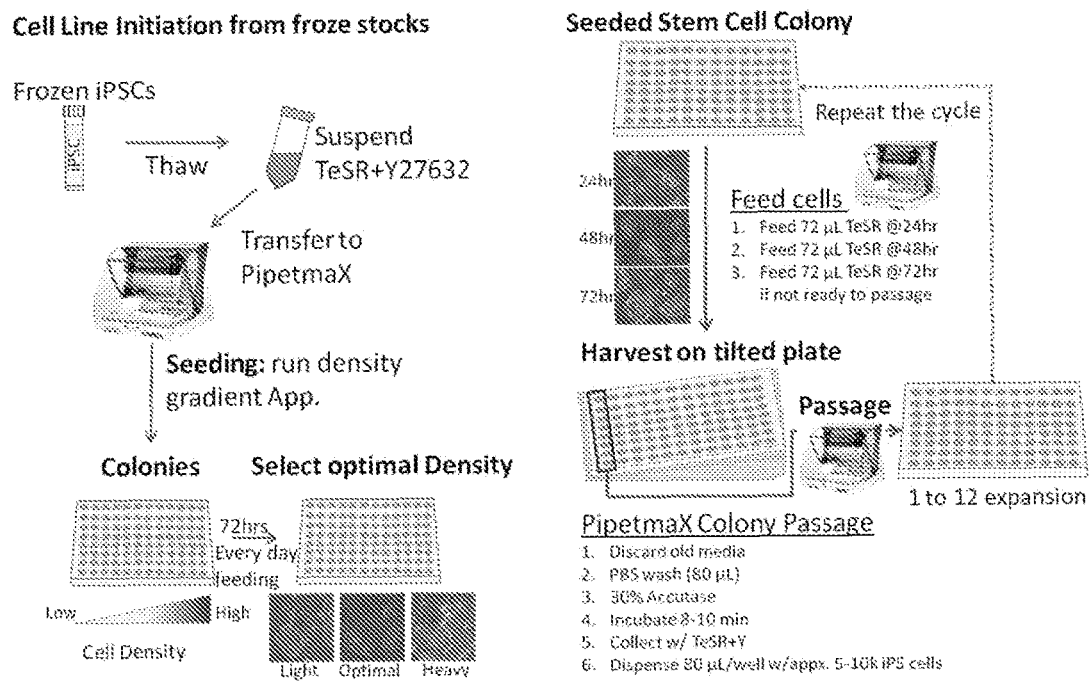
FIG. 3 is a schematic diagram of an automated stem cell culture system.

In general the procedures herein may be carried out by a robotic liquid handling system (such as the PipetmaX™ system mentioned above or other robotic liquid handling systems). In some embodiments, additional robotic devices may be used, e.g. to move components to and from the robotic liquid handling system. For example, an external robotic system may be used to move multi-well culture plates from a cell culture incubator to the robotic liquid handling system in order to perform one or more protocols such as feeding, passaging, or harvesting of cells. The external robotic system may also be programmed to move supplies such as empty plates or pipette tips from a repository onto the robotic liquid handling system and/or may be able to dispose of used materials. In certain embodiments, a single robotic system may handle the functions of the robotic liquid handling system as well as the additional functions of the external robotic system as described herein. FIG. 3 shows a diagram of an automated cell culture system, demonstrating how the system can be used to initiate a cell line from a frozen stock (FIG. 3, left) as well as how ongoing cultures can be used to seed additional wells of a multi-well plate (FIG. 3, right). FIGS. 6-17 show diagrammatic overviews of various automated stem cell handling procedures in accordance with various embodiments.

Robotic liquid handling systems may be used for high-throughput synthesis and biological or biochemical screening which includes, but is not limited to, mixing and reacting of small fluid samples of various chemical and biological entities. An important advantage of standard robotic liquid handling systems is that they simultaneously handle a plurality of liquid samples, for example 8 or 12 liquid samples may typically be handled simultaneously in parallel. Accordingly, liquid handling robots have been especially useful when performing biological or diagnostic assays, PCR, DNA synthesis, or combinatorial chemistry. Standard robotic liquid handling systems are used by a variety of companies when performing these many liquid handling protocols including QIAGEN, Illumina, IDT, Invitrogen, Sigma-Genosys, and MWG Biotech.

Robotic liquid handling systems may be used with standard reaction well plates including, for example, 24-, 48-, 96-, or 384-well plates, although other types and sizes of plates may be used. The multi-well plates may have plastic or glass bottoms and the wells may be round, square, or other shapes. Such plates are positioned on the top/back of the liquid handling robot, generally on a bed designed to hold one or more plates or other components. The bed may include, for example, nine positions for holding one or more of a multi-well plate, a multi-channel trough (e.g. for holding media or cell suspensions during procedures), clean pipette tips, a disposal container for used pipette tips and/or waste liquids, and an angled adapter to hold a multi-well plate (FIGS. 18-28). The bed may have other numbers of positions, e.g. 12, 16, etc. The bed may be movable in x, y, and z directions. In some embodiments, the bed may move in a horizontal plane (e.g. which may be designated as the x and y directions) which may facilitate mixing of solutions in any of the containers on the bed. In one particular embodiment, the bed may be moved in a direction parallel to a long axis of a trough, e.g. of a multi-channel trough, to mix the contents of the trough. If the trough includes a cell suspension, the mixing action helps keep the cells in suspension at a relatively uniform density while aliquots of cell suspension are collected and distributed to multi-well plates.

The robotic liquid handling system may also include a movable multi-channel pipette head which may be used to aspirate and then dispense various fluids among the various wells of the reaction well plates. The multi-channel pipette head may have 4, 6, 8, 10, 12, or other numbers of pipette nozzles. Movement of an independently operable positive displacement syringe is typically used to aspirate or dispense liquid from the various liquid nozzles, although other mechanisms may also be used.

While many of the embodiments disclosed herein were carried out using the Gilson PipetmaX™ automated liquid handling robot, other robotic liquid handling systems may also be used provided that the system includes a movable multi-channel pipette head that is used for liquid handling as well as a mechanical manipulation capability. In general, the pipette head is movable in three orthogonal axes (designated x, y, and z) with respective motor positioners. In various embodiments, the pipette head may be moved along any of the axes with an accuracy of at least 10 µm, at least 5 µm, at least 2 µm, at least 1 µm, at least 0.5 µm, or at least 0.1 µm. Pipette head motion may controlled by a computer control system via a control unit; the computer control system and control unit may be located in the pipette head, in the body of the robotic liquid handling system, or remote from the system. The head may also incorporate a camera used to perform machine vision functions, such as bar code reading of multi-well plates. The head may be movable over the main bed of the apparatus on which multi-well plates and other biological sample containers are placed. In various embodiments the functions of the robotic liquid handling system may be carried out by a controller, which may be part of the computer control system.

An application software program (app) may be developed as part of the disclosed system, where the software program carries out methods according to various embodiments of the invention. The software program directs the robotic liquid handling system to carry out procedures (for example the procedures outlined in FIGS. 5A-5F) in an automated manner with little or no user interaction required. In some embodiments the system may be completely automated insofar as an external robotic system may be capable of moving materials to and from the bed of the robotic liquid handling system; in other embodiments user interaction may be required, for example to set up the bed of the robotic liquid handling system prior to a particular procedure and to remove materials following completion of the procedure.

Figure 18:
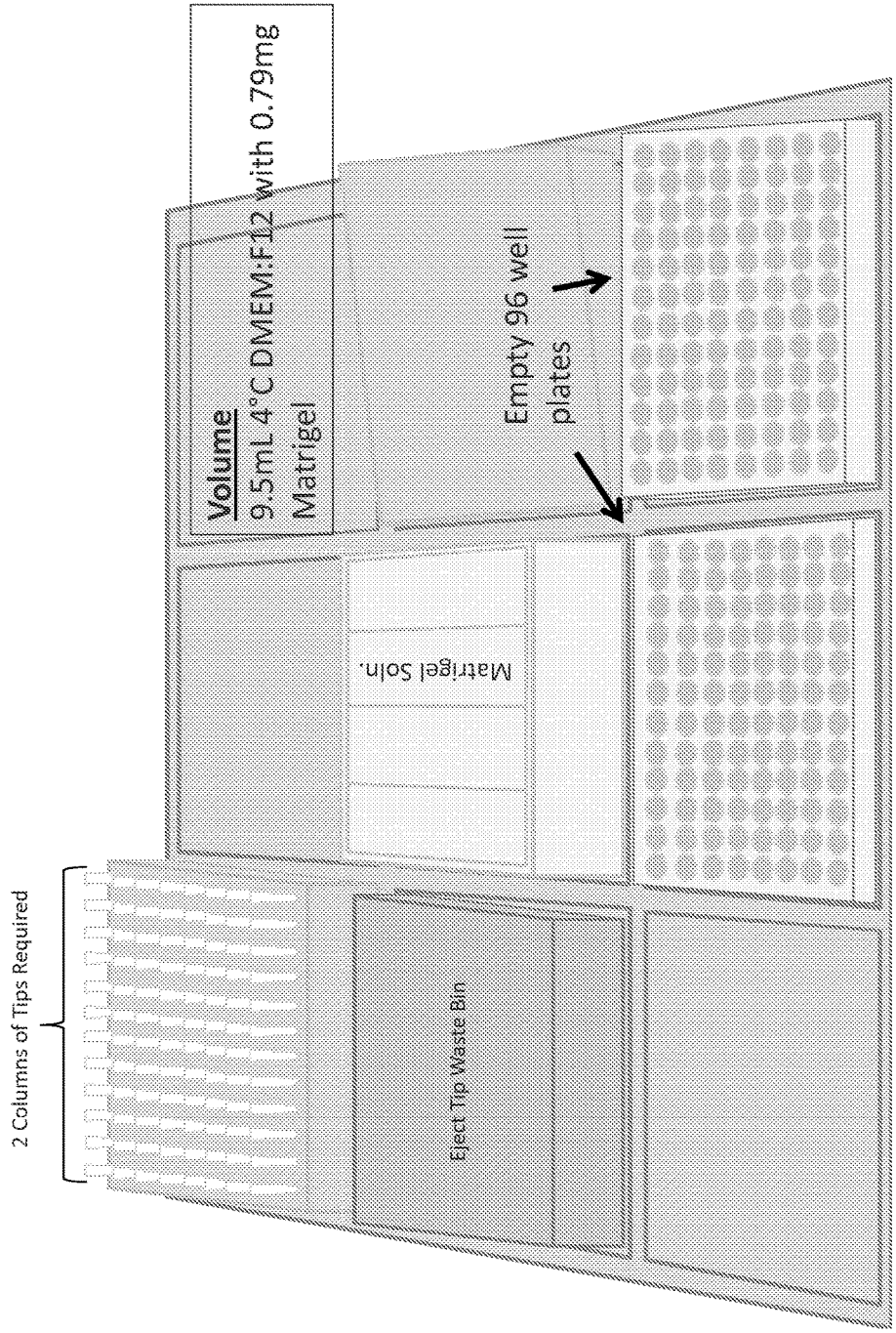
FIGS. 18-28 show various arrangements of materials on a bed of a robotic liquid handling system during different procedures.
Figure 19:
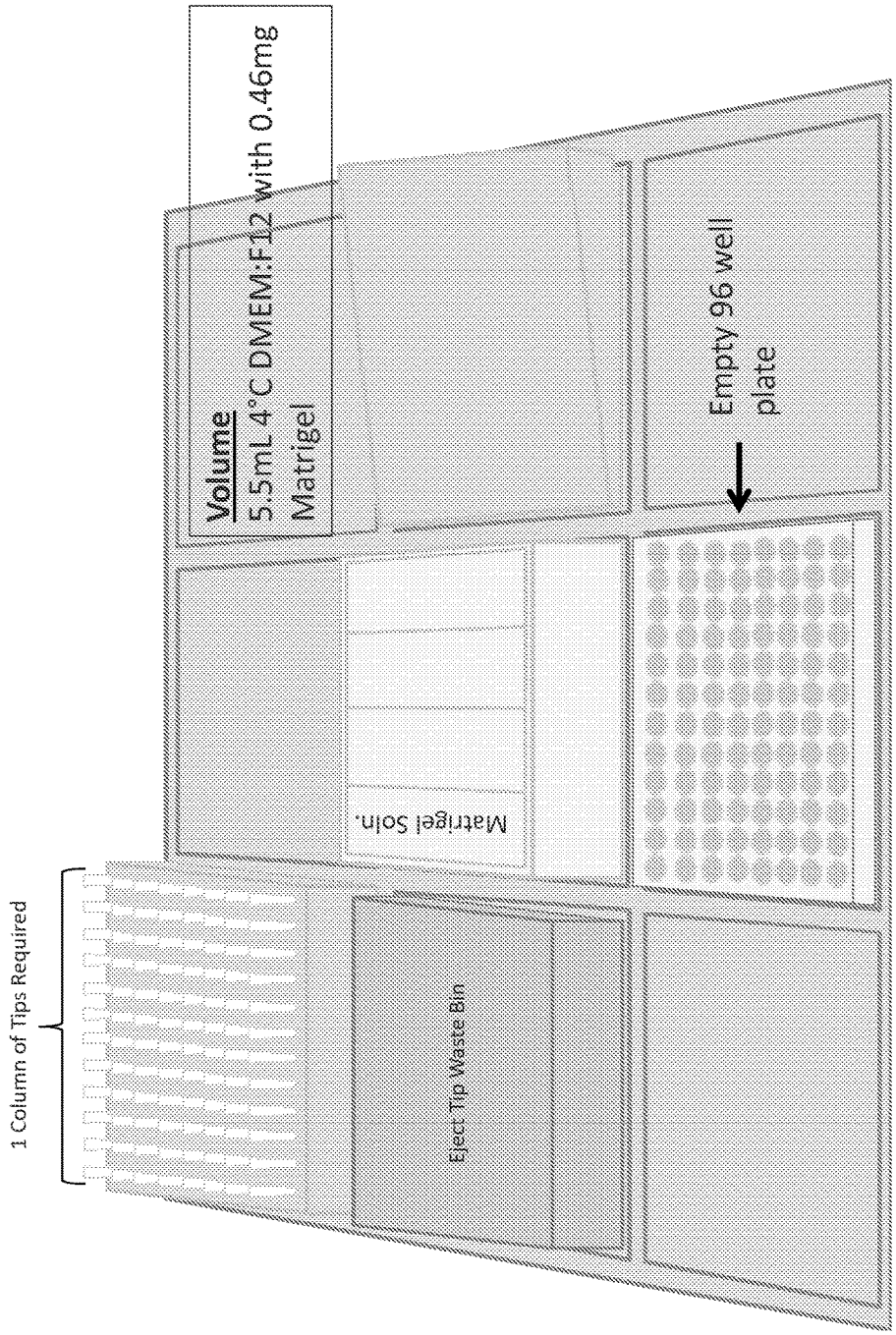

FIGS. 18-28 show various arrangements of materials on a bed of a robotic liquid handling system during different procedures. For example, FIG. 18 shows a starting arrangement of materials prior to application of extracellular matrix material (such as Matrigel) onto two multi-well plates. In the upper left bed position is a container of clean pipette tips; in the left middle position is a container for collecting used pipette tips; in the center middle position is a multi-trough plate (a four-channel trough is shown, although troughs with other numbers of channels may be used), where one or more trough contains solutions needed for the procedure (e.g. extracellular matrix material/Matrigel); in the right middle position is an angled adapter, which is not used for the procedure of FIG. 18; and in the lower middle and right positions are empty multi-well plates. The software application is programmed to guide the multi-channel pipette head to each of the bed positions, adjusting the head to the correct x, y, and z coordinates with an appropriate acceleration and speed for each task, to apply extracellular matrix material to each of the wells, to wait for a predetermined incubation period to allow attachment of the matrix material to the wells, and to conduct a series of wash steps following incubation. In various embodiments, a user or an external robotic system locates items on the bed as shown in FIG. 18 prior to execution of the software routine for conducting extracellular matrix application procedure. In other embodiments, a user or an external robotic system locates items on the bed as shown in FIGS. 19-28 prior to execution of the software routines for conducting other procedures. When the procedure is complete the robotic system or user would set up the bed for another procedure; no user interaction is required while the procedure is being carried out. FIG. 19 shows a bed setup for applying matrix material to a single multi-well plate.

Figure 20:
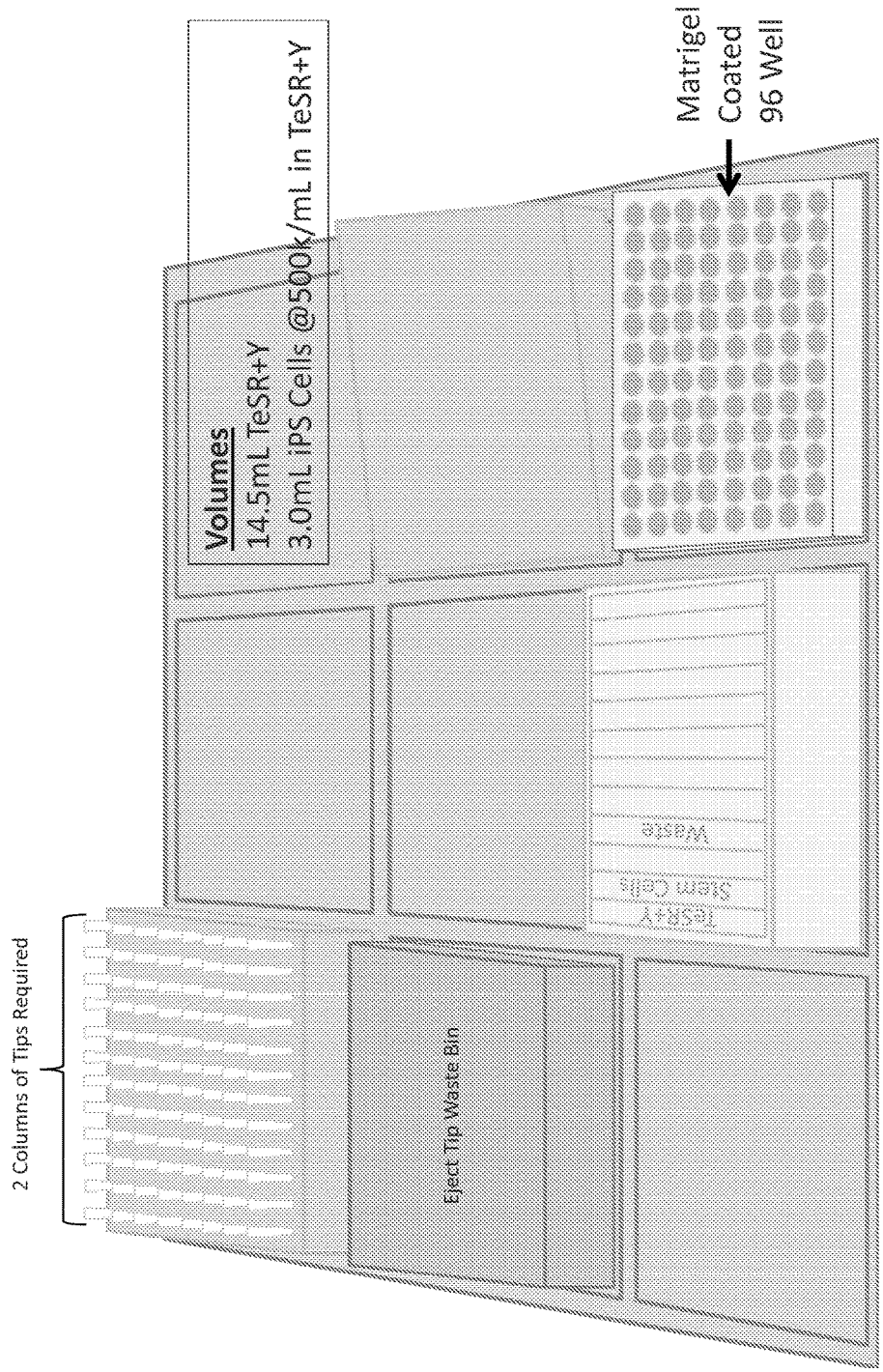

FIG. 20 shows a bed setup for plating stem cells in wells of a multi-well plate at a variety of densities (a gradient). In this embodiment the multi-channel trough plate includes twelve channels, where one channel includes cell culture media (such as mTeSR+Y27632), another channel includes a suspension of stem cells, and another channel is designated for collection of waste solution. In this setup the lower right bed position has a multi-well plate in which the wells have been coated with extracellular matrix material (such as Matrigel).

Figure 21:
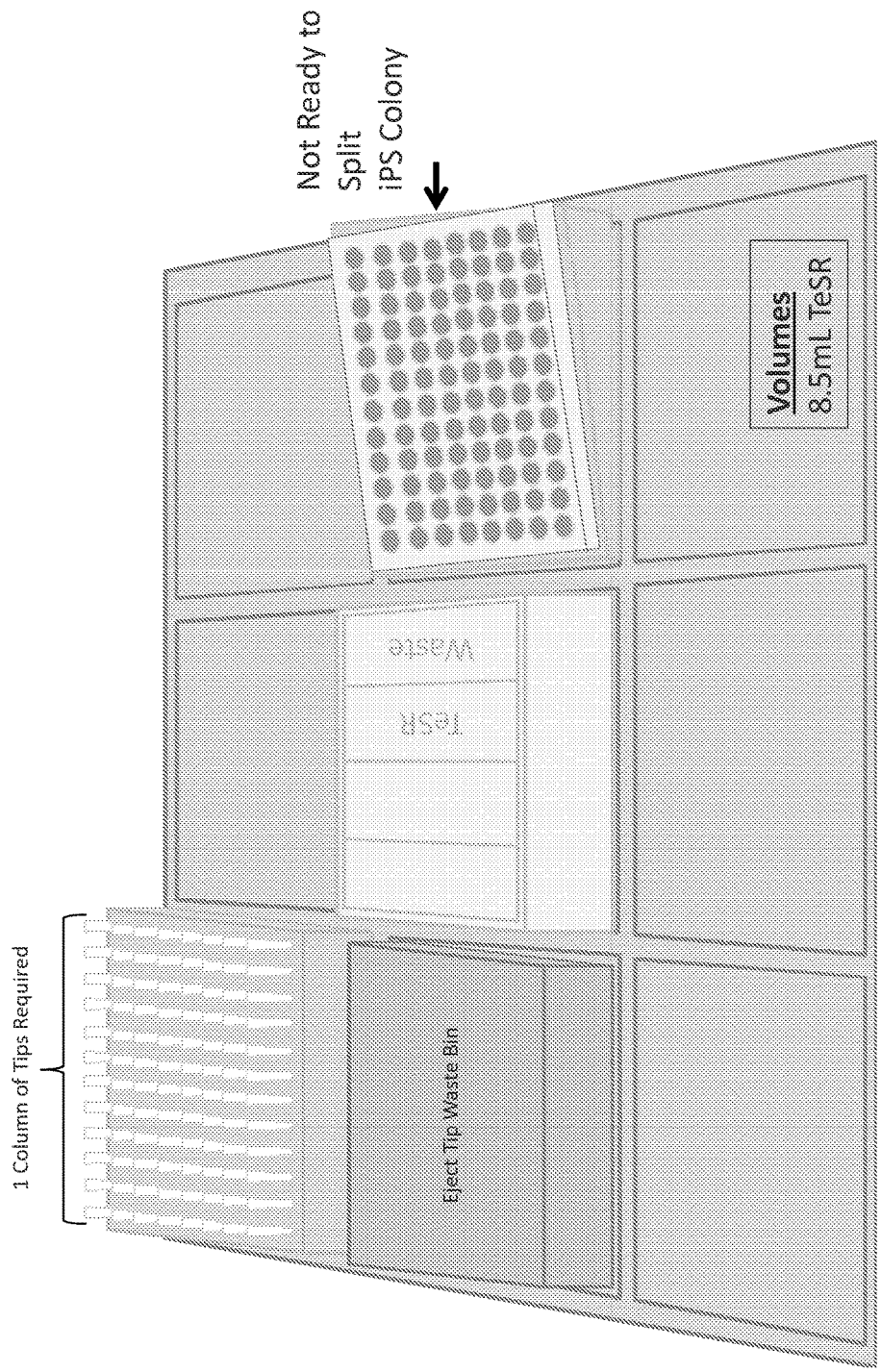

FIG. 21 shows a bed setup for stem cell feeding. In embodiments such as this, the multi-well plate containing stem cells may be located on the angled adapter, as shown, to facilitate removal of a greater amount of cell culture media from the wells, making each wash step more complete. One of the troughs of the multi-channel trough plate in this embodiment contains fresh media (such as mTeSR1) while one or more other troughs are designated for collecting waste.

Figure 22:
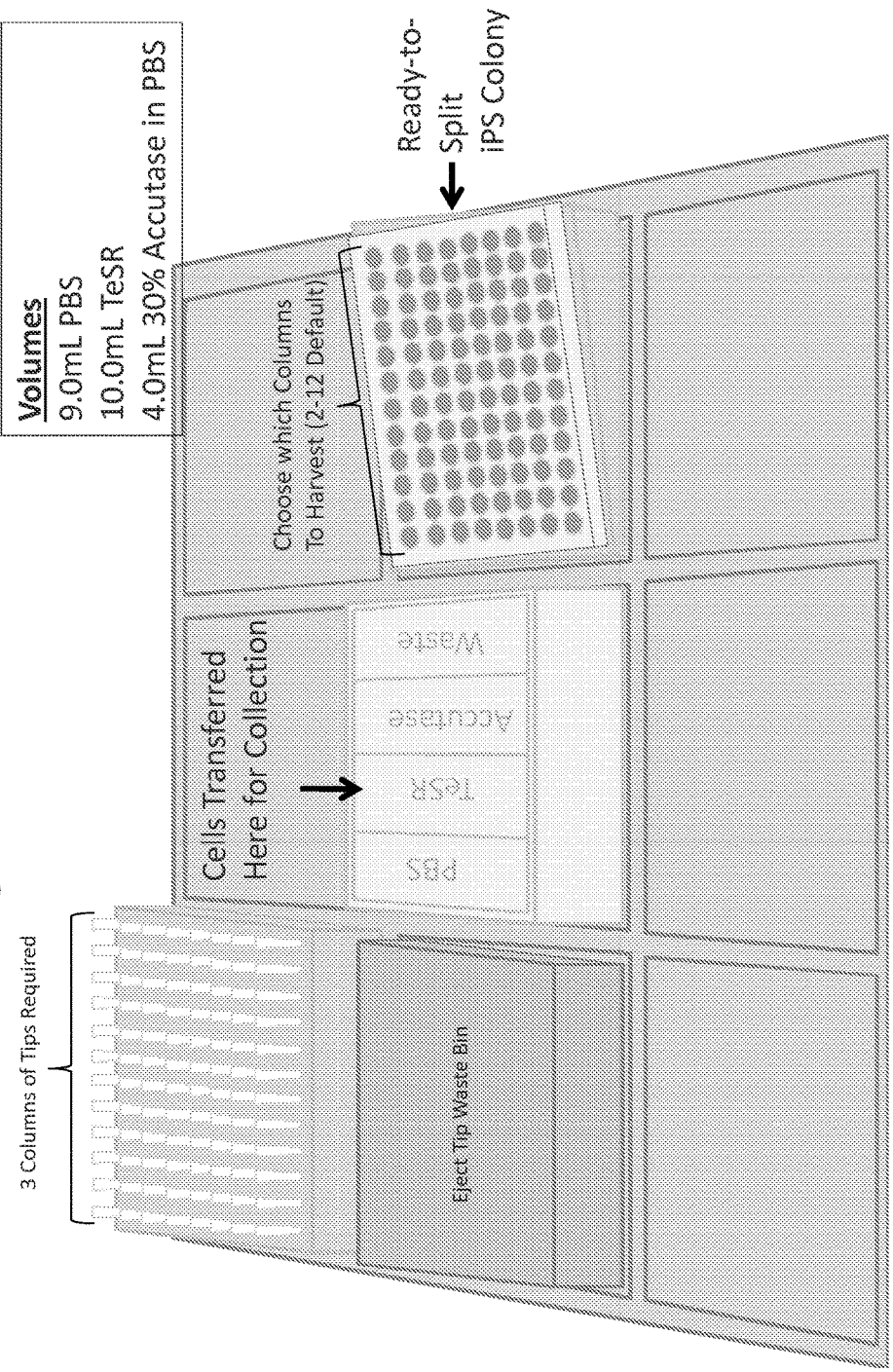
Figure 23:
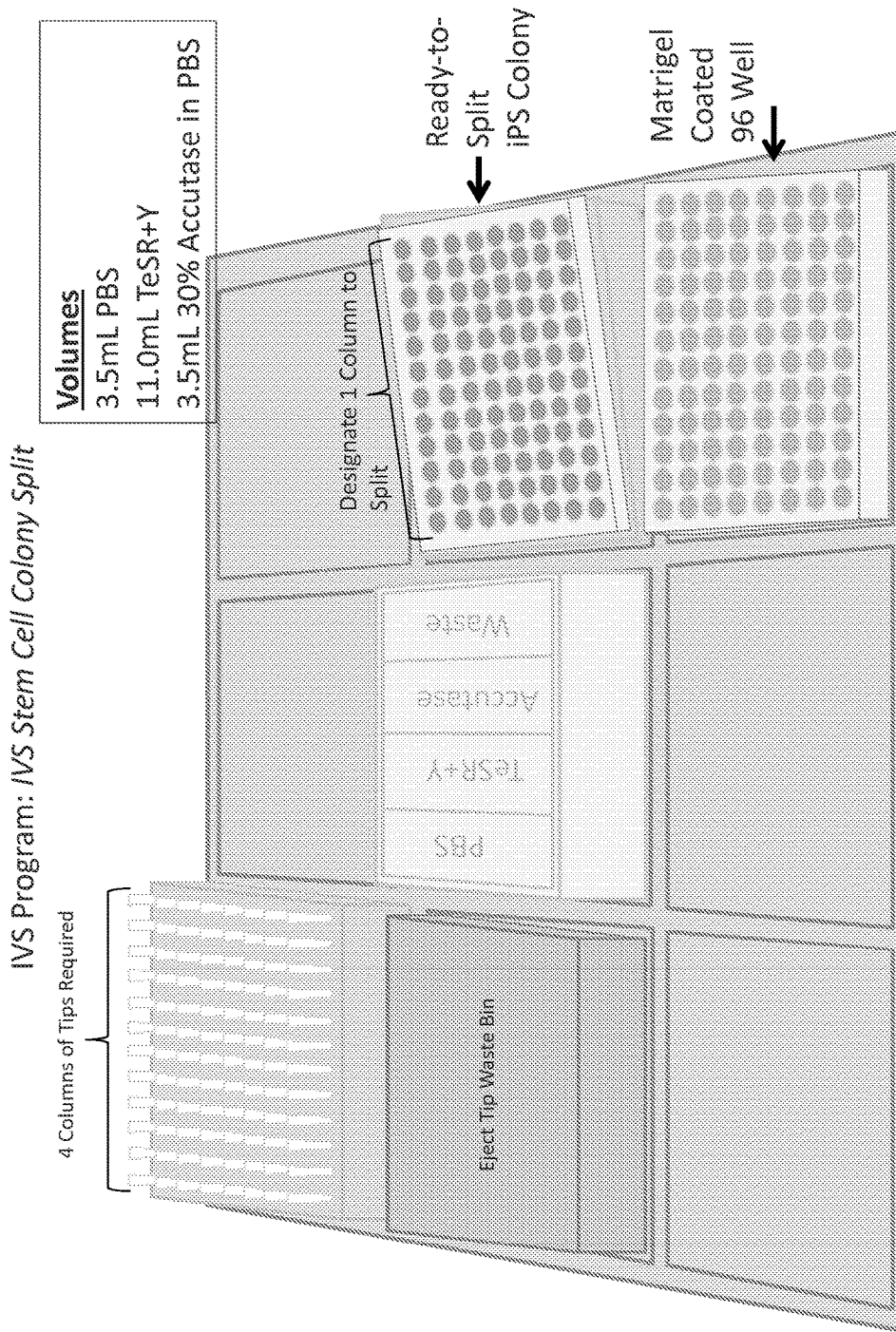
Figure 24:
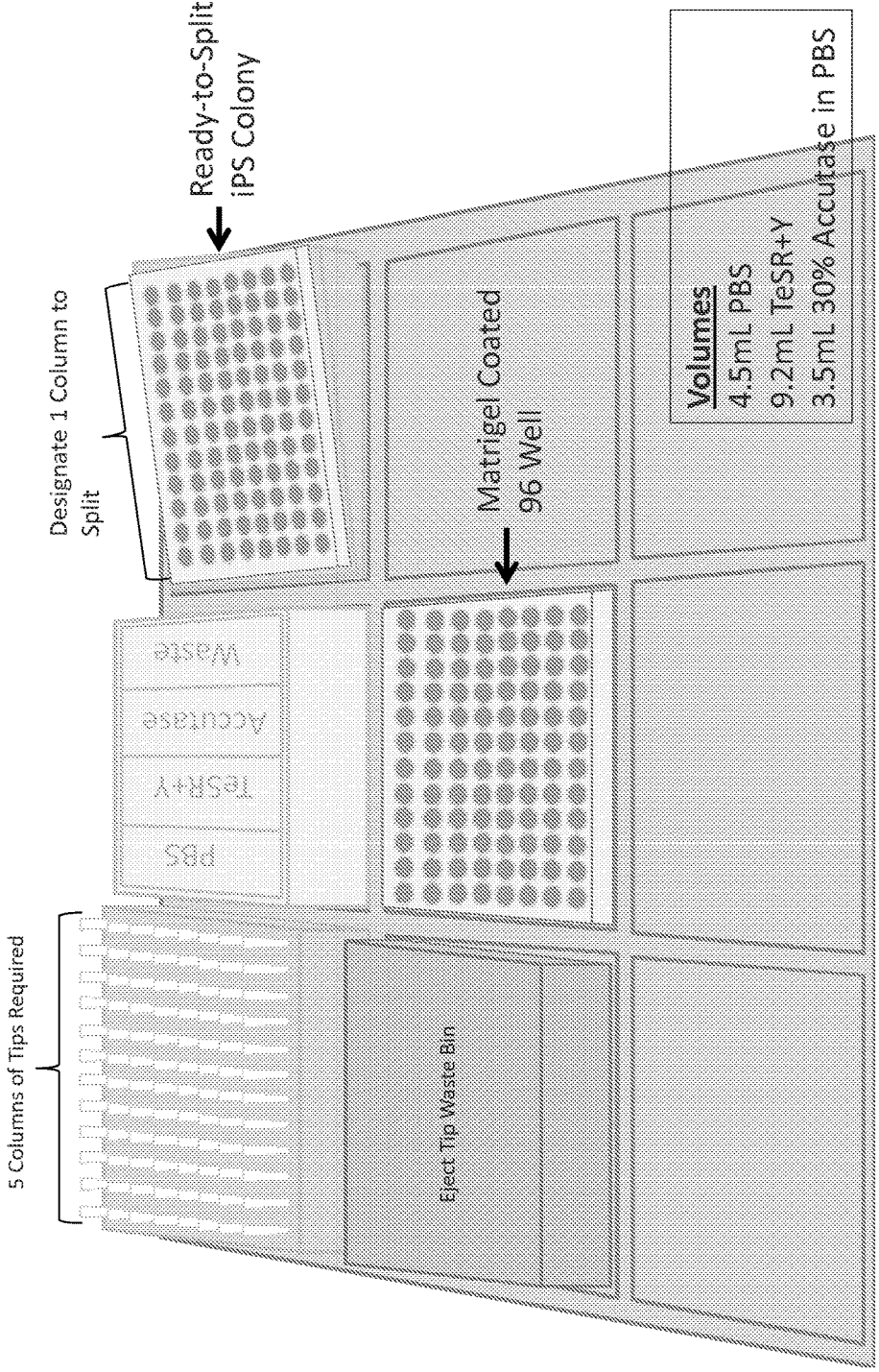
Figure 25:
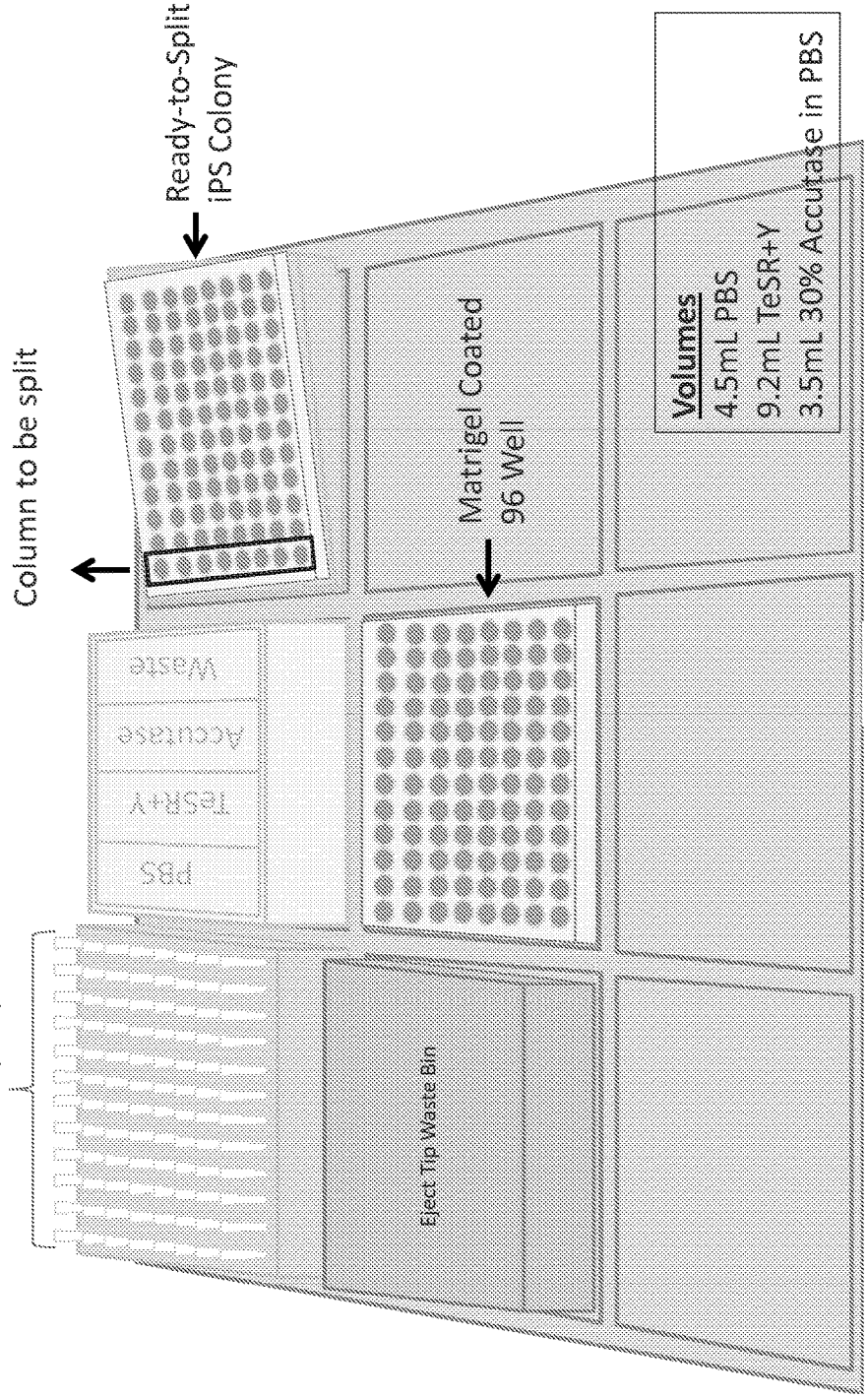
Figure 26:
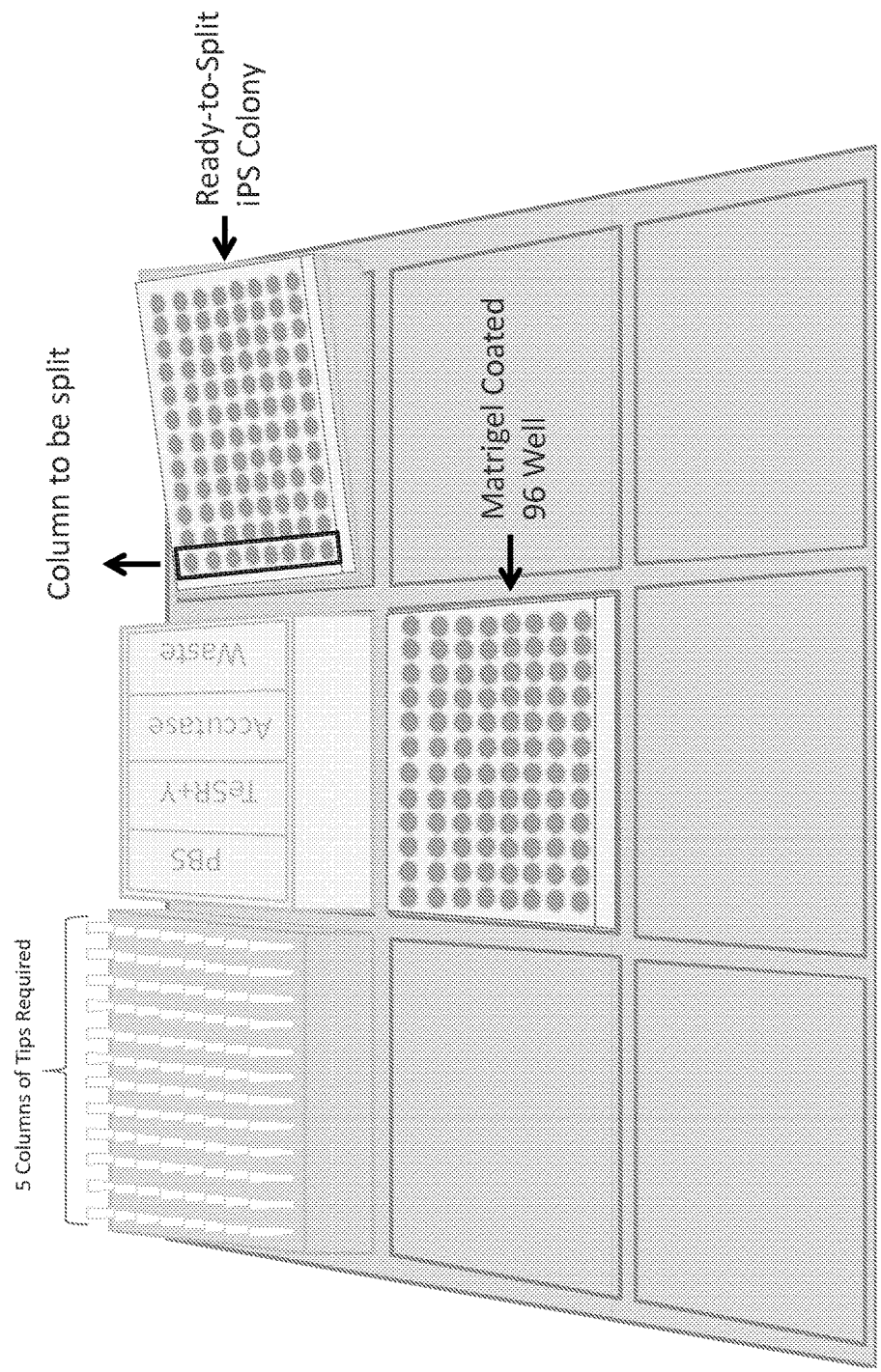
Figure 27:
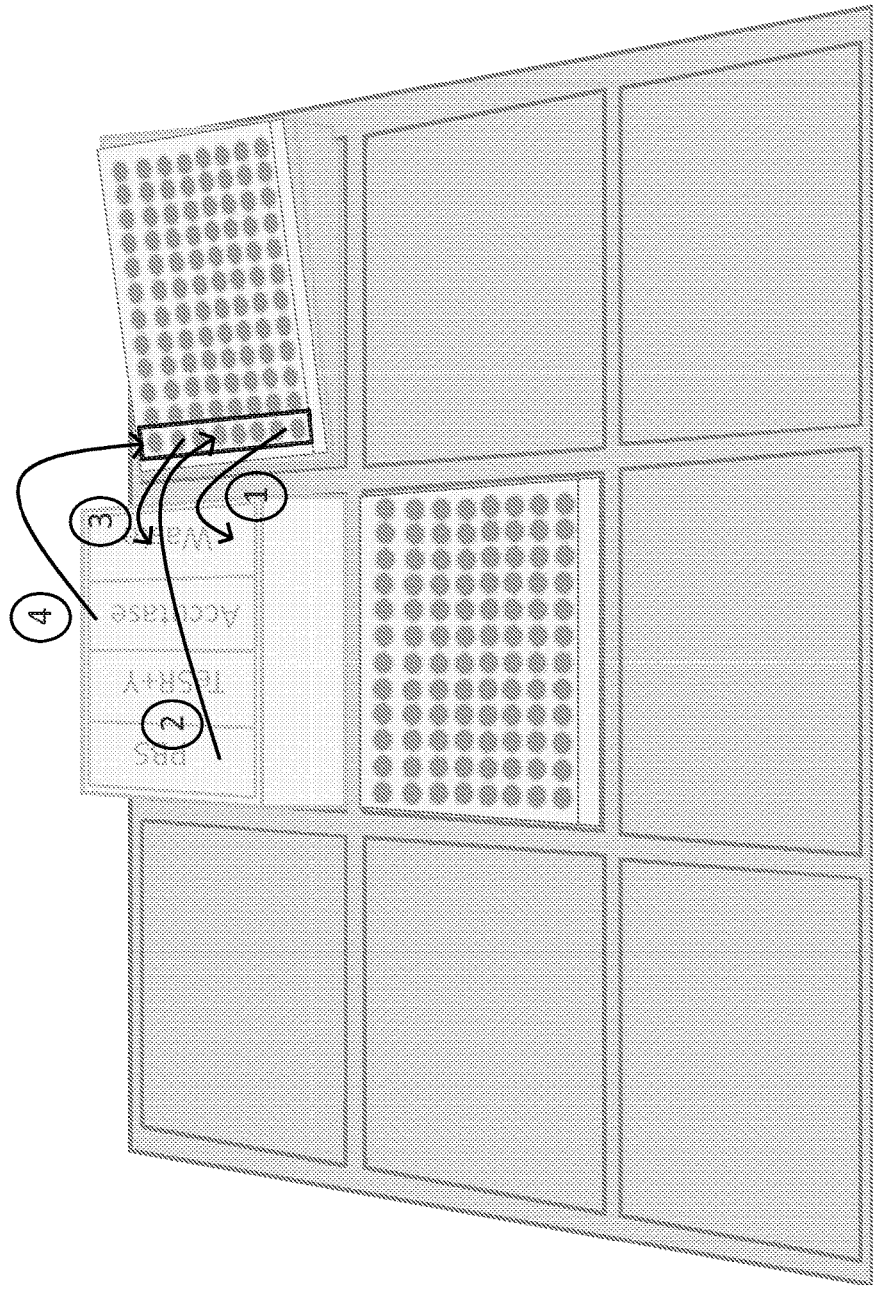

FIG. 22 shows a bed setup for harvesting stem cells from a multi-well plate. The multi-well plate is located on the angled adapter to optimize changing of solutions and recovery of detached cells. The troughs of the multi-channel trough plate include saline solution (PBS), cell culture media (mTeSR1), enzyme solution for detaching cells (Accutase®), and a waste trough. Following the harvest procedure the cells may be frozen into aliquots or distributed onto other cell culture plates. FIG. 23 shows a bed setup for splitting of stem cell cultures. The bed setup is similar to that of FIG. 22 but also includes a multi-well plate that has been pre-treated with extracellular matrix material, so that the harvested cells can be distributed into the wells of this plate.

Figure 28:
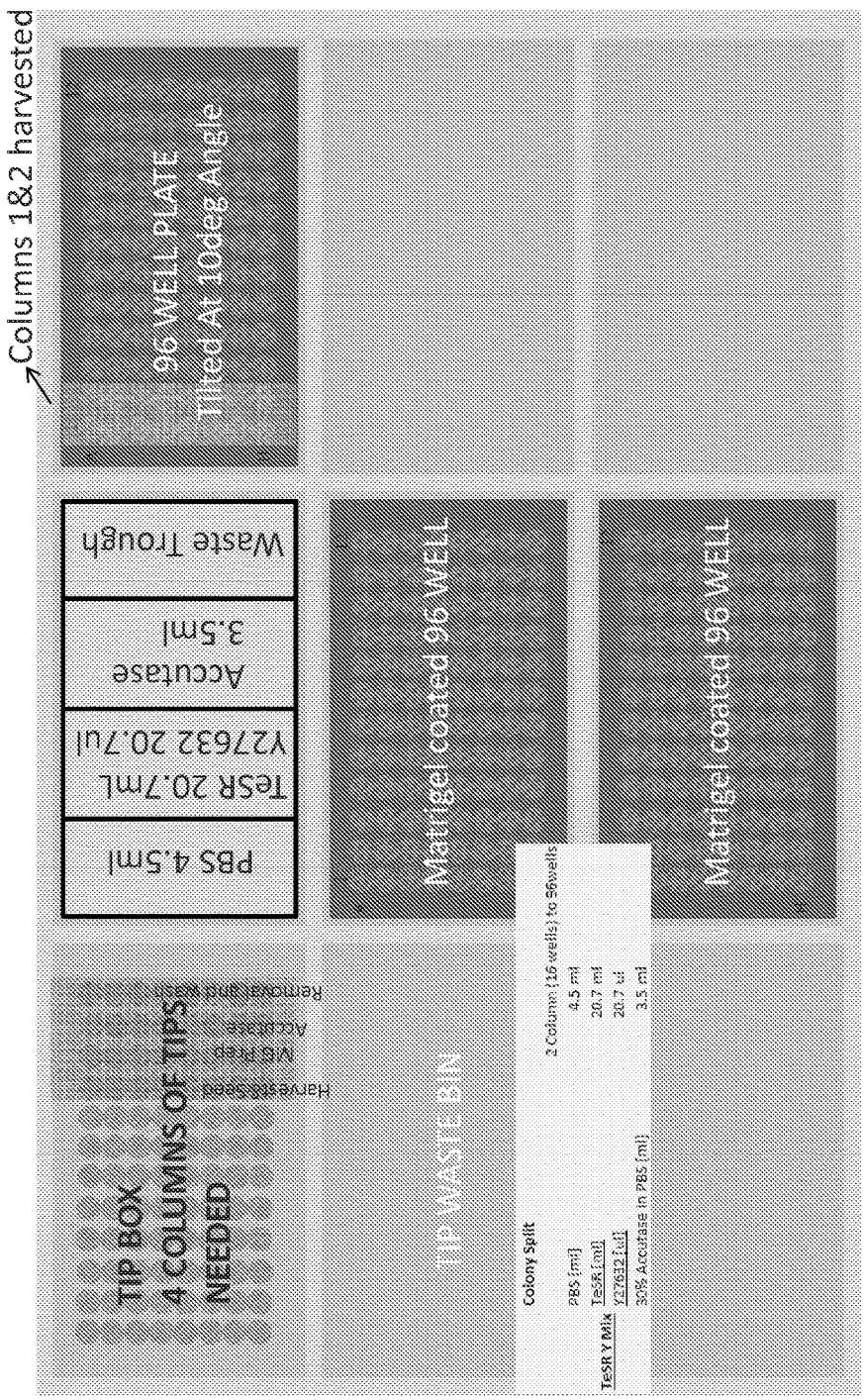

FIGS. 24-28 show bed layouts for splitting of stem cells. Although different ratios of splitting may be used, in these examples the cells are split in a 1:12 ratio. The stem cells in one "column" of wells (e.g. 8 consecutive wells of a 96-well plate) are removed and redistributed evenly into twelve columns of wells on a fresh multi-well plate that has been pre-treated with extracellular matrix material; in some embodiments two columns of cells are distributed to two multi-well plates (FIG. 28). The remaining columns of cells from the first plate may be put to various uses, such as for preparing frozen aliquots of cells for later use or for inducing differentiation. Essentially each well of cells is dissociated (e.g. using an enzyme such as Accutase®, as described herein) and redistributed into twelve similar-sized wells on a new plate; other splitting ratios are also possible. As described herein, the combination of titrating the amount of enzyme to a low level during cell dissociation and diluting the enzyme-containing cell suspension greater than two-fold following dissociation and cell recovery, the inventors have determined that this procedure can be performed without the need for a centrifugation step, thereby allowing the procedure to be automated.

In some embodiments, the protocols, including for suspension cultures, may require optimization through iterative procedures to be adapted to different cell lines. In addition, it has been observed that different types of media and supplements used for stem cell culture may alter the efficiency (0-90%) of subsequent differentiation (e.g. into cardiac myocytes) using small molecules. Since iterative optimization processes for suspension cultures require large media volumes, such procedures will increase capital investment required for scale-up cell productions, including for the relatively large quantity of reagents such as the small molecules needed to induce differentiation. Therefore, an ability to flexibly modify protocols with less and fewer materials will dramatically reduce the cost of cell productions. A similar flexibility will facilitate development and expansion of stem cell (e.g. iPSC) lines reprogrammed from different patients for personal applications (e.g. for personal medicine and autologous cell/tissue implants). The disclosed approach uses hydrogel polymer-coated, such as Matrigel-coated, multi-well (e.g. 96-well) plates and the automated cell culture system is able to screen a large number of cell culture conditions to identify the best condition for maintaining pluripotency. Using the optimized set of conditions, the same multi-well plate format can be used to scale up stem cell production and achieve a cost-effective automated culture system for use in the stem cell and other industries.

In some embodiments, once a protocol is optimized using the multi-well format, the liquid handling robot can faithfully replicate the optimized cell culture conditions without requiring further modification, e.g. for different size dishes, since optimization and subsequent culturing can be carried out using multi-well plates. By varying supplements, media, and other cell handling protocols, including cell passage methodologies, culture conditions can be customized for a specific stem cell (e.g. iPSC) line reprogrammed from a specific patient, followed by mass production of that patient's stem cells in an efficient and rapid manner.

Applications of stem cells in personalized drug efficacy and toxicity testing would require rapid expansions of stem cells reprogrammed from a number of patients. Applications such as these also require a large number of cells to be obtained quickly. Thus, having the capacity to expand many personalized stem cell lines in parallel would facilitate performing personalized drug efficacy and toxicity testing using patient-specific stem cell lines. The cost and time of stem cell expansion can be greatly reduced by eliminating the conversion steps of protocols from screening/optimization to scale-up production, as disclosed herein.

Using the systems and methods disclosed herein, starting up new stem cell colonies from frozen stocks can be initiated by seeding the stem cells in wells of a multi-well plate at a preprogrammed range of cell seeding densities; in various embodiments the wells may be coated with an extracellular matrix material (e.g. Matrigel) prior to cell seeding. The density of colonies is visually inspected in a range of 24-96 hours (e.g. 72 hours) after seeding to select an optimal density and to start cycles of stem cell colony maintenance. For example, a user may visually compare cell density in one or more wells with images of light, optimal, and heavy cell/colony densities and based on which image matches the desired density a particular well will be selected for further processing. In various embodiments, the user may use an interface of the robotic liquid handling system to indicate which well(s) contain cells of a desired density that should be selected for further processing.

For example a user may select a heavy density well for splitting or an optimal density well for conducting differentiation; the light density wells may be cultured for an additional period of time (e.g. 24-72 hours) until the cells reach a desired density level. In various embodiments, desired density level may correspond to a level of growth at which the well or dish contains less than 15-20% of cell-free space (i.e. cells occupy 80-85% of the available growth surface) and/or at a point in time when almost all of the cell colonies are about to connect to each other (see Ludwig, T. E., et al., Feeder-independent culture of human embryonic stem cells. Nat Meth, 2006. 3(8): p. 637-646, incorporated by reference herein). In certain embodiments, heavy cell density would be more dense than this desired or medium level and light density would be less dense than this desired or medium level.

In addition to or instead of visual inspection and comparison to reference images, cell density may be evaluated in other ways, for example by detaching cells and running samples through a cell counter, by plating cells on a counting slide, or by using an imaging-based counting mechanism (e.g. image/pattern recognition). In the maintenance mode, growth of colony sizes is inspected every 12-48 hours (e.g. 24 hours) to determine a suitable time for passaging the stem cells (FIG. 3, right panel). For example, in one particular embodiment a human fibroblast-derived iPSC line (System Biosciences) was passaged every 72 hours at an expansion rate of 12-fold.

To detach cells from the multi-well plate during passages, colonies are incubated at an elevated temperature (e.g. 37° C.) with an optimized concentration of an enzyme such as a protease to promote cell detachment (e.g. Accutase®; Life Technologies) and are divided into smaller aggregates, for example distributed into new wells of a multi-well plate at varying ratios. The cells may be divided at ratios of 1:2 (i.e. a group of cells from one well may be distributed into two wells), 1:3, 1:4, 1:5, 1:7, 1:10, 1:12, 1:15, 1:20, or other suitable ratios. At some points (e.g. when initially plating an aliquot of recently-thawed cells) it may be desirable to create a gradient of cell densities in order to select a desired density for further cell growth. In one embodiment, individual wells or rows of wells each receive a different density of cells from a suspension of cells in order to create a density gradient. To create wells of varying density, different volumes of cell suspension can be added to each well, followed by a suitable amount of cell culture media to fill the wells.

In certain embodiments, this passage protocol eliminates the need for a centrifugation step by reducing enzyme activities to a negligible degree by diluting the enzyme-containing solution with enough mTeSR1. That is, during incubation the concentration of enzyme is at a level that is sufficient to detach cells, however once the enzyme-containing solution is diluted 2-fold or more (include dilutions of 3-, 5-, 7-, 10-, or 20-fold or more) the enzyme is no longer effective. In one embodiment, the enzyme Accutase is used at a concentration of 30% (v/v) during the cell detachment procedure and after dilution is at a final concentration of 0.34% (v/v), at which concentration it is no longer effective for inducing cell detachment. Holding the multi-well plate in a tilted rack allows the robotic liquid handling system to collect ~99% of medium without damaging cells. The pipette tip positions are controlled at sub-micron precision to perform complex liquid handling protocols to minimize cell damage and distribute cells equally to each well (e.g., using media dispensing on side walls, continuous gentle mixing of suspended cells). In various embodiments, other enzyme or chemical treatments may be used to loosen and/or detach cells from culture plates such as wells of a multi-well plate, including trypsin, collagenase, or EDTA (Ethylenediaminetetraacetic acid), to name a few.

In various embodiments, the angle at which the multi-well plate is placed is between about 5° and about 20°, and in one particular embodiment is 10°. To maintain the multi-well plates at a desired angle, an angled adapter may be used which is designed to hold one or more standard sized multi-well plate at a given angle. The base of the adapter may be designed to be the same size and shape as the base of a multi-well plate so that the adapter can fit into holders that are designed to hold the multi-well plates. Placing the multi-well plate at an angle during procedures that require dissociation of cells from the dish provides several advantages insofar as a greater amount of fluid can be removed from each well. Prior to addition of enzyme-containing solution to the dish, most (about 99%) of the culture fluid can be removed so that the enzyme-containing solution is not significantly diluted when it is added to each well. In addition, when detached cells are aspirated from each well, a higher percentage of fluid and cells is recovered from each well.

Setting the multi-well plate at an angle facilitates fluid recovery from each well by pooling the fluid on one side of each well and by making it easier for the pipette tips to be guided to the lowest point of the fluid pool (i.e. the lowest point of the tilted wells). Due to the generally tapered shape of the pipette tips along their entire length plus in some cases an additional narrower taper near the end, it may be difficult to maneuver the opening at the end of the pipette tip to a location at or near the bottom edge of each well, since the wider portions of the pipette tend to hit the edges of the wells before the opening can be placed near the edge at the bottom of the well. However, by tilting the dish not only does the fluid pool to one side of the well but also the tip opening can be located at or near the lower edge of the well without hitting the sides of the wells. In various embodiments, the robotic liquid handling system is capable of guiding the openings at the ends of the pipette tips to within less than 20 μm, less than 10 μm, less than 5 μm, or less than 1 μm of the lowest edge of the tilted wells.

Figure 29:
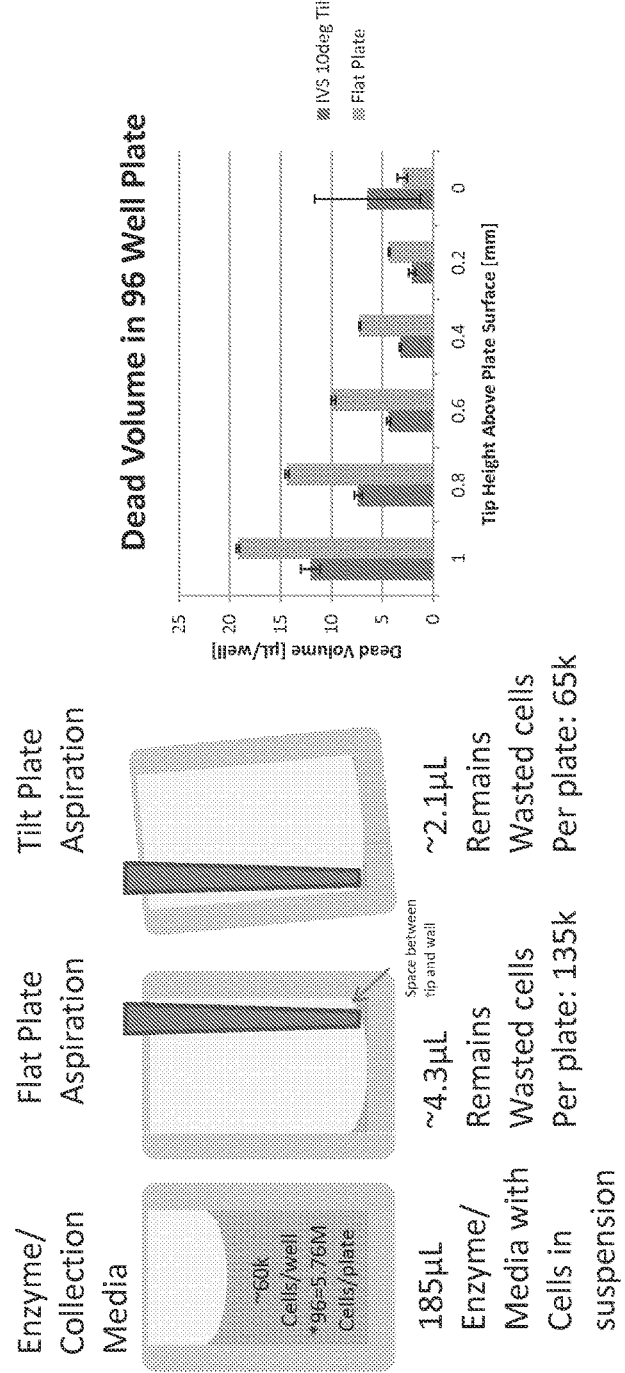

FIGS. 29-33 show diagrams of features of the disclosed methods and systems, in particular features which contribute to successful automation of stem cell handling. FIG. 29 shows how tilting the multi-well plates improves fluid recovery, using a 96-well plate as an example. Starting with 185 μl of fluid, about 4.3 μl remains in a well when the plate is level. However, tilting the plate permits greater fluid recovery so that only about 2.1 μl remains after fluid recovery. FIG. 29 also shows the "dead volume" (volume of fluid remaining in a well following a fluid recovery step) in a 96-well plate as a function of the height of the pipette tip above the plate surface, showing that at nearly every height the tilted plate has a greater degree of recovery and therefore a lower dead volume.

Figure 30:
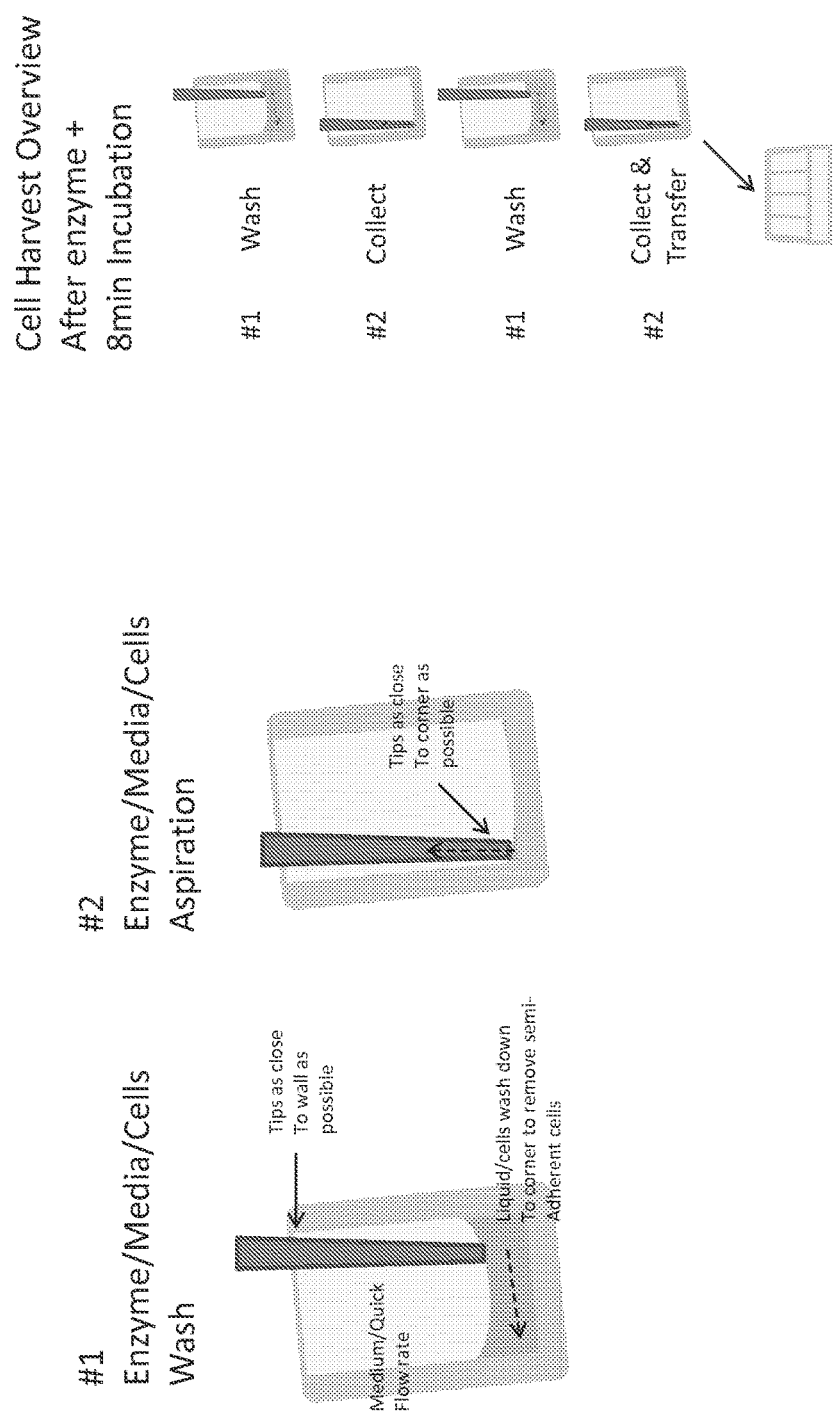

FIG. 30 shows how tilting the multi-well plate improves recovery of cells. To add solutions or media, the pipette tip is guided to a location as close as possible to the wall of the well on the "high" side and fluid is then dispensed. The opening at the end of the pipette tip may be at various levels above the bottom of the well, although in general it is desirable to locate the opening within less than 1 mm (or less than 0.5 mm or less than 0.1 mm) to minimize damage to cells from fluid flow. The movement of fluid across the surface in a "downhill" direction towards the lowest point in the tilted well helps loosen and remove cells during dissociation procedures, e.g. following treatment with a chemical or enzyme to detach cells from the surface of the well. In some embodiments (FIG. 30, right) the fluid in a well may be collected on the "low" side of the well and re-dispensed on the "high" side (which may be repeated one or more times) in order to loosen and dislodge cells to maximize recovery while not subjecting cells to overly-harsh fluid flows which could damage the cells.

Figure 31:
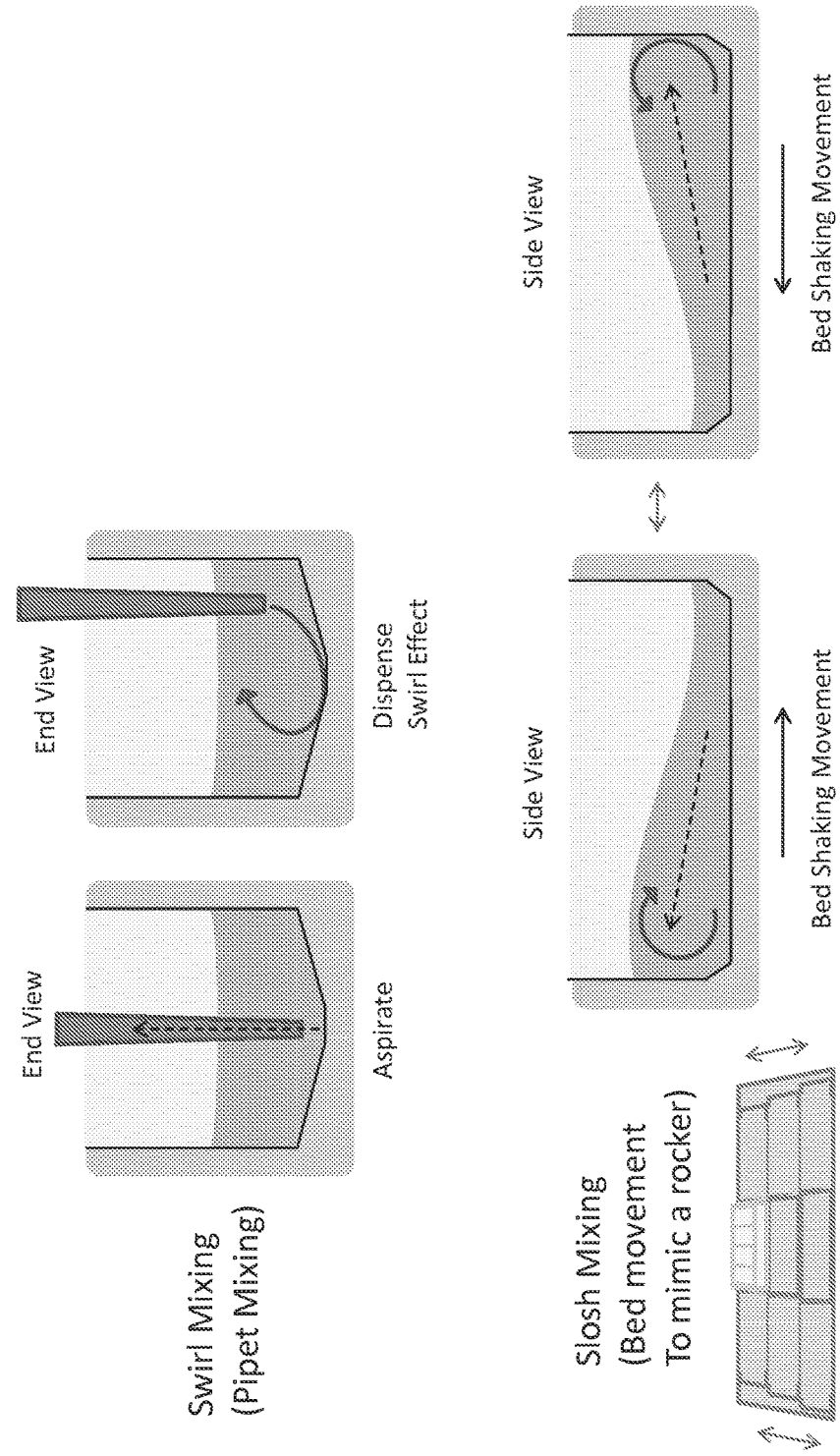

FIG. 31 shows procedures for mixing fluids in a trough of a multi-channel plate. The pipette may be used to mix the contents of the trough, e.g. fluid may be aspirated in the deepest central part of the trough and dispensed in a location towards the shallower sides to provide a gentle swirling motion which mixes the contents of the trough. The bed may also be translated, e.g. back and forth in a linear motion that is parallel to the long axis of the trough, to provide a gentle mixing motion. These mixing motions may be useful when plating suspensions of cells, namely to maintain the cells in suspension at an approximately uniform concentration.

FIG. 32 shows advantages of tilting the multi-well plates for fluid recovery. In addition to the fact that the fluid is accumulated into a smaller space, tilting also permits the pipette tip to be guided to a location closer to the bottom edge of the well where the base and the sides of the well meet. Due to surface tension of the media, more fluid accumulates in this bottom edge region. Without tilting of the plate, the tapered shape of the pipette prevents the opening of the tip from being located close to the bottom edge. With tilting, the tip can be guided very close to the edge to maximize fluid recovery. In various embodiments the opening at the end of the pipette tip may be located within less than 0.5 mm, less than 0.1 mm, or less than 0.05 mm from the side and/or bottom surface of the well.

Figure 33:
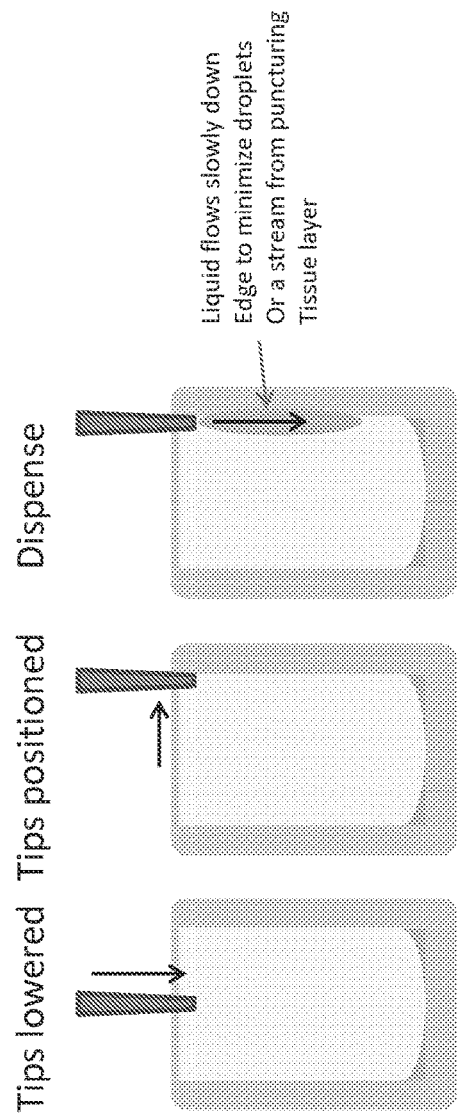

FIG. 33 shows how pipette tips can be guided to the sides of wells of a multi-well plate when dispensing liquids into the wells in order to introduce fluids in a manner that causes little or no disruption to the cells in the well. This procedure may be used during feeding steps while culturing pluripotent stem cells and also while culturing differentiating cells. Certain differentiated cell types (e.g. cardiac myocytes) must grow a confluent sheet of cells as part of the differentiation process; careful handling of the cells, including the fluid introduction procedure of FIG. 33, is important for allowing the cells to properly differentiate without disrupting the cell layer.

In various embodiments, the multi-well plates may be kept at an elevated temperature (e.g. 37° C.) while they are being treated with enzyme such as a protease to promote cell detachment, a procedure that may last for 5-30 minutes (typically about 10 minutes). To facilitate maintaining the cells at the elevated temperature while the cells are being handled by the robotic liquid handling system, in some embodiments the angled adapter may be heated so that the multi-well plates do not have to be returned to a cell culture incubator during enzyme treatment. In various embodiments, the angled adapter is heated using a resistive heating mechanism (e.g. embedded in the adapter or on a surface that contacts the multi-well plate) or a fluid heating mechanism (e.g. heated liquid or air may be circulated inside the adapter). Suitable mechanisms may be included to maintain the angled adapter at a desired temperature. For example, a thermocouple or other temperature measurement device may monitor the temperature of the adapter and/or the multi-well plate to provide feedback for adjusting heat input in order to maintain the desired temperature, such as 37° C.

The multi-well culture plate format serves as a discovery tool as well as scale-up tool through use of the robotic liquid handling system. In various embodiments, these methods were used to test high-throughput optimization protocols of iPSC expansion using different media and supplements. The protocols described herein were used with at least two iPSC lines reprogrammed from human dermal fibroblasts (System Biosciences, Inc.) and adipocytes (Applied Stem Cell, Inc.), respectively. The stem cells were tested to confirm maintenance of pluripotency based on the generally accepted methodologies known to those skilled in the art. Furthermore, an automated system has also been established to produce cardiac myocytes (CMs) differentiated from human iPSCs for fabricating engineered heart tissues for drug discovery research. Differentiation of the stem cells into CMs may be induced by modulation of the Wnt signaling pathway, using either genetic approaches or with suitable small molecule agents (see Lian et al., PNAS 109 (27): E1848-E1857, incorporated herein by reference in its entirety).

In various embodiments, cultured pluripotent stem cells are cultured under conditions intended to promote differentiation of the cells into a particular cell and/or tissue type. Factors which may drive or at least influence differentiation of pluripotent stem cells into a particular cell or tissue type include cell density, addition of compounds (e.g. small molecule drugs) to the culture solution, or introduction of one or more genes into the cells. In addition to the introduction of genes or compounds, achieving a certain cell density may promote differentiation, particularly for certain cell types (e.g. cardiac myocytes) which require cells to grow to a uniform sheet of confluent cells or sometimes multiple overlapping sheets of cells in order to differentiate.

Further, the present inventors have observed that pluripotent stem cells have a greater likelihood of differentiating when they are located in a region of a cell culture dish or well that is closer to a vertical edge of the dish or well, for example in a band that is about 5 mm to about 8 mm from the outer edge of the dish or well. Accordingly, use of a multi-well plate with more wells having smaller well sizes (e.g. plates with 24, 48, 96, or 386 wells, or larger numbers of wells) has the advantage of most or all of the cells undergoing differentiation. Therefore, in certain embodiments stem cells are grown and differentiated in dishes or wells having a bottom surface area (i.e. surface area for growth) of no more than about 1.9 cm$^2$ (e.g. 24 well plate having wells each with a base diameter of 15.6 mm), no more than about 0.95 cm$^2$ (e.g. 48 well plate having wells each with a base diameter of 11.0 mm), or no more than about 0.32 cm$^2$ (e.g. 96 well plate having wells each with a base diameter of 6.4 mm). In various embodiments the bottom surface area is at least about 0.3 cm$^2$, at least about 0.4 cm$^2$, at least about 0.5 cm$^2$, at least about 1.0 cm$^2$, at least about 1.5 cm$^2$, or at least about 2.0 cm$^2$. In other embodiments, the bottom surface area is less than about 2.5 cm$^2$, less than about 2.0 cm$^2$, less than about 1.5 cm$^2$, less than about 1.0 cm$^2$, less than about 0.5 cm$^2$, less than about 0.4 cm$^2$, less than about 0.3 cm$^2$, or less than about 0.2 cm$^2$. The ratio of the circumference of the base of the well to the surface area of the well gives an indication of how much of the cell growth area is near an edge. Thus, in some embodiments the ratio of the circumference of the base of the well to the surface area of the well is about 0.26 (for a well of a 24-well plate), about 0.36 (for a well of a 48-well plate), or 0.63 (for a well of a 96-well plate). In various embodiments, the ratio is at least 0.2, at least 0.3, at least 0.4, at least 0.5, at least 0.6, at least 0.7, at least 0.8, at least 0.9, or at least 1.0.

In some embodiments cultured stem cells are differentiated into cardiac myocytes, as described herein. In other embodiments, cultured pluripotent stem cells may be differentiated into skeletal muscle cells, kidney tubule cells, red blood cells, gut smooth muscle cells, lung cells (alveolar cells), thyroid cells, pancreatic cells, epidermal skin cells, neuronal cells, or pigment cells.

Although differentiation of stem cells into a particular cell or tissue type is of interest, in many instances the pluripotent stem cells must be grown under conditions that maintain the cells' pluripotency without differentiating. Thus, in various embodiments stem cells are cultured under conditions that are designed to maintain the cells' pluripotency, i.e. conditions that do not promote differentiation into any particular cell type. One or more tests may be performed to determine whether the stem cells have maintained pluripotency, as discussed below.

First, the morphologies of colonies are evaluated to identify any unusually shaped colonies ("good" colonies have flat, well-defined edges with homogeneous cell types). Then, the expression of pluripotency markers, such as Oct4 and Nanog, as well as surface markers, such as stage-specific embryonic antigen-4 (SSEA-4) and TRA-1-60, are analyzed by staining with fluorophore-conjugated antibodies (Millipore). If samples are positive for expression of one or more of the markers, the sample is tested for its alkaline phosphate expression level using a staining kit (Millipore). Results are documented using an inverted fluorescent microscope with an image capturing system (Nikon Eclipse TS100-F, Q-Imaging CCD Camera).

In some embodiments, samples expressing pluripotency markers are sent to service providers to examine teratoma formation and karyotypes. A standard testing of teratoma formation takes ~7 weeks by service providers (e.g., Applied Stem Cell, Inc.). In various embodiments, two samples from each batch are tested.

Other pluripotency tests may be used in parallel with teratoma formation and karyotyping. One such test, PluriTest, is a cost-effective and animal-free method to determine pluripotency and is based on interrogation of large scale datasets of genome-wide somatic and pluripotent expression profiles. For the tests, Illumina HT12 array chips (which contain 12 different samples on one chip) are used and the array is analyzed using the iScan System (Illumina). Using this system, multiple samples (3-4) collected from different wells from a single batch process are run to identify and characterize potential variability between different wells. Thus, using these and other tests for pluripotency, data may be obtained to confirm the pluripotency of stem cells (e.g. iPSC lines) cultured using the disclosed methods and systems, including with the use of multi-well culture plates in a robotic liquid handling system.

Figure 4:
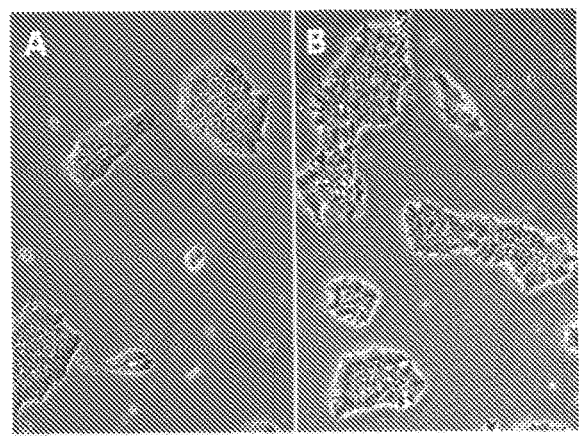
FIG. 4 shows pluripotent stem cells cultured in (A) mTeSR1 and (B) E8 media.
Figure 5A:
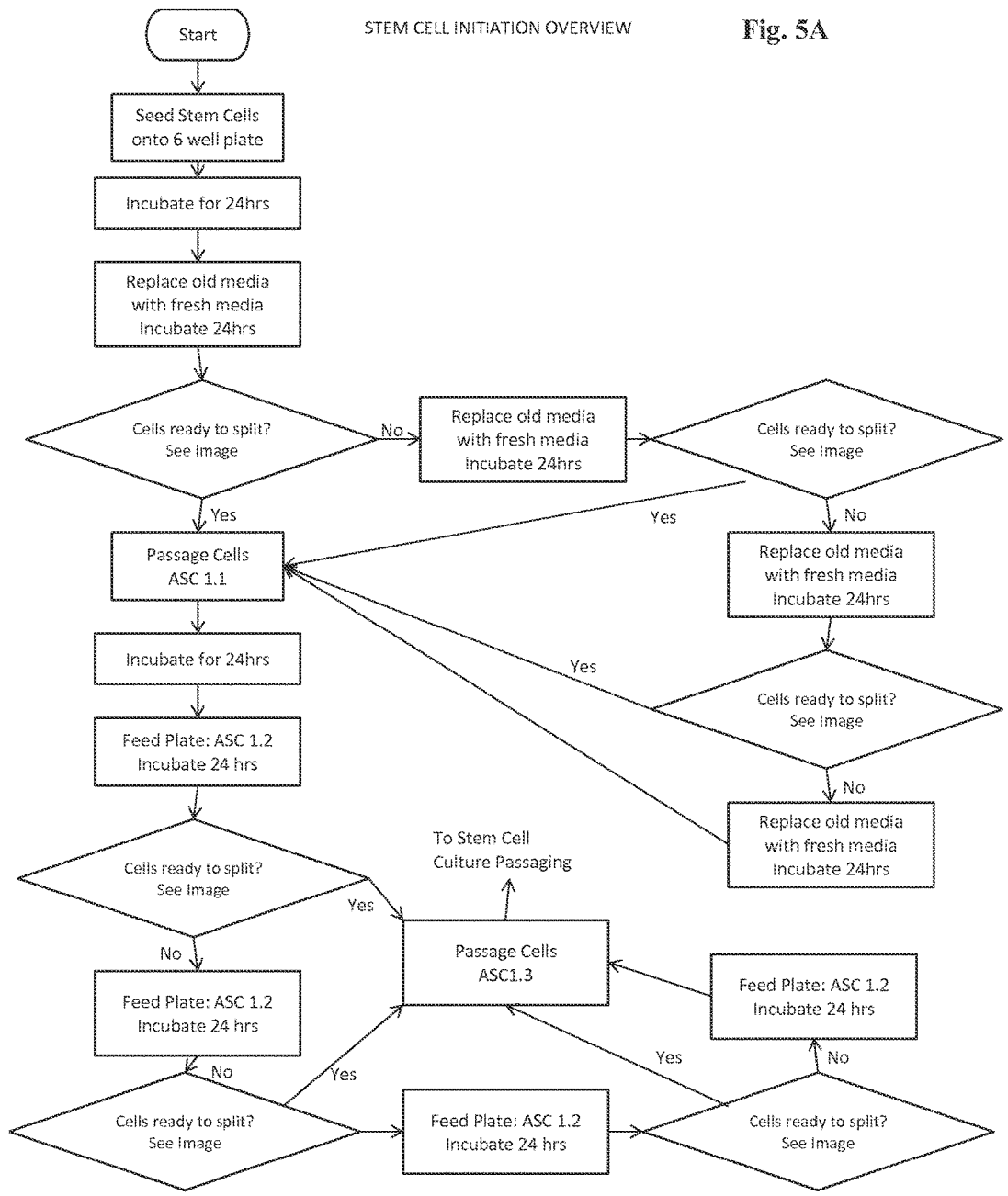
Figure 5C:
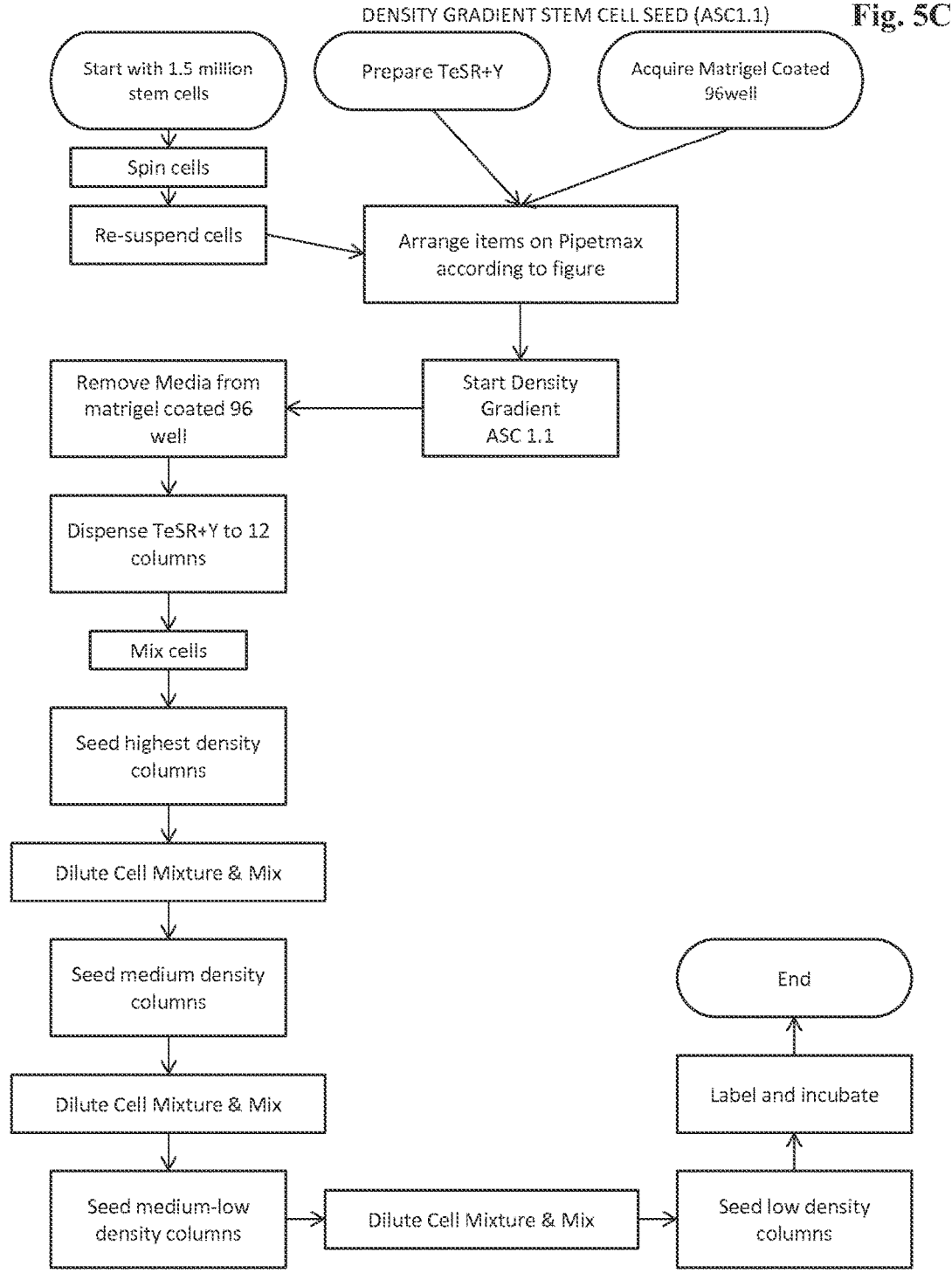
Figure 5D:
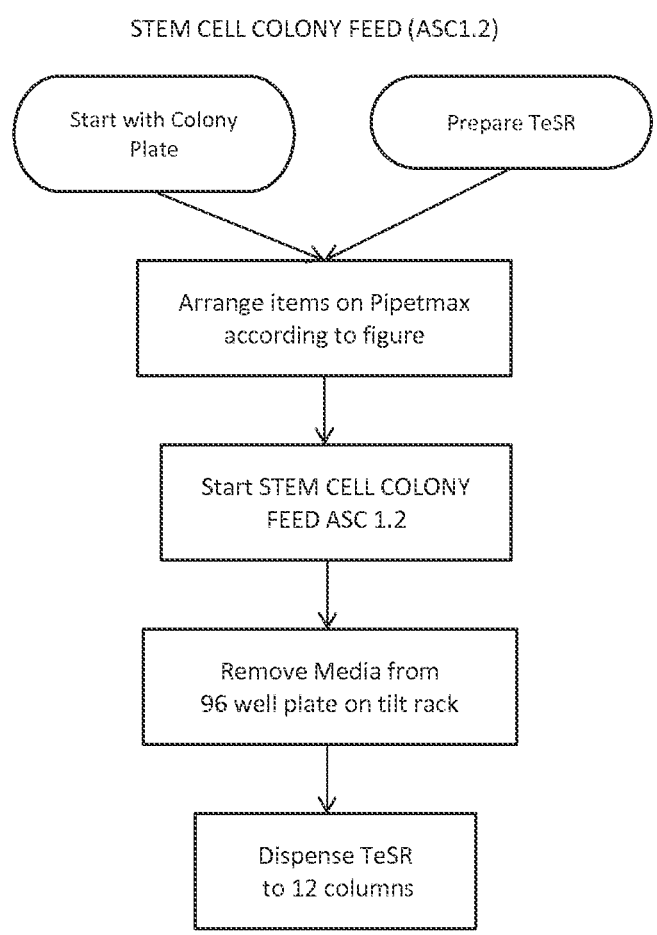
Figure 5E:
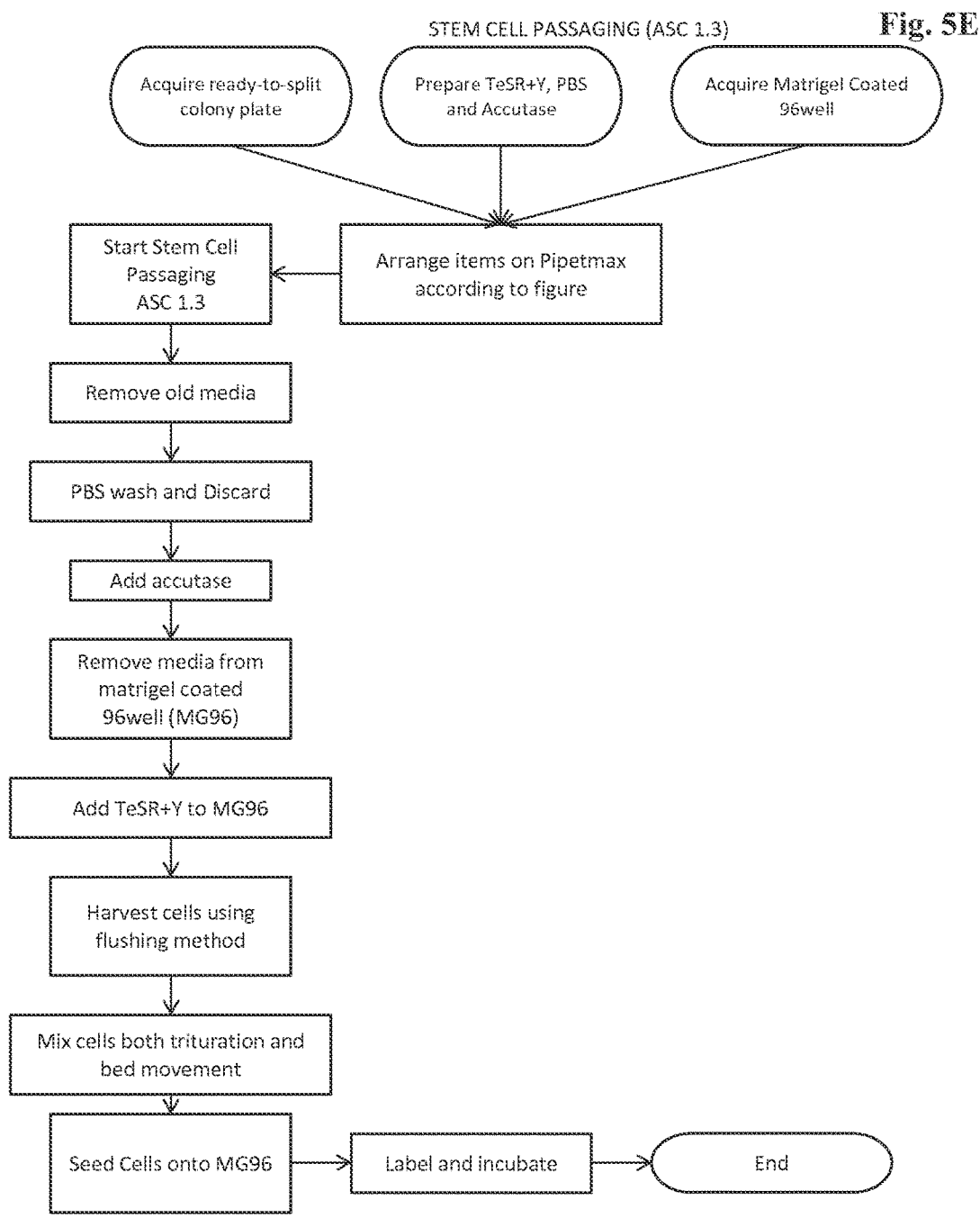
Figure 5F:
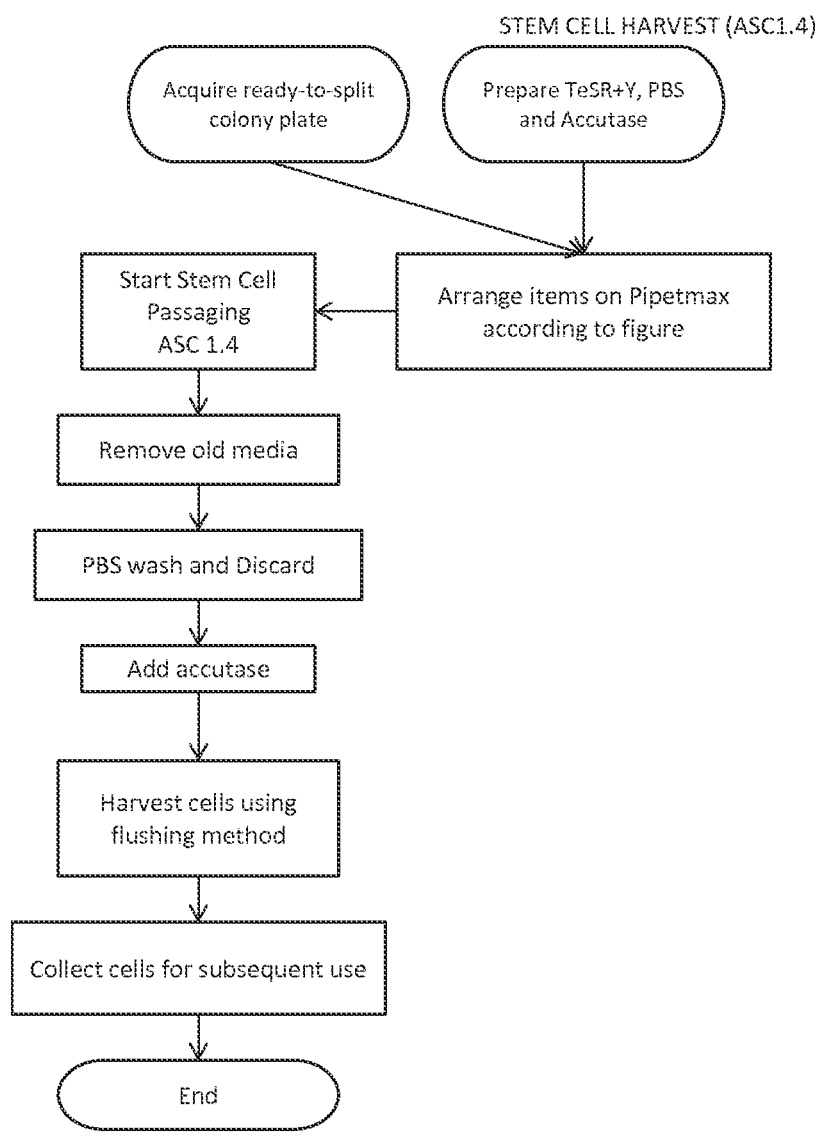
Figure 6:
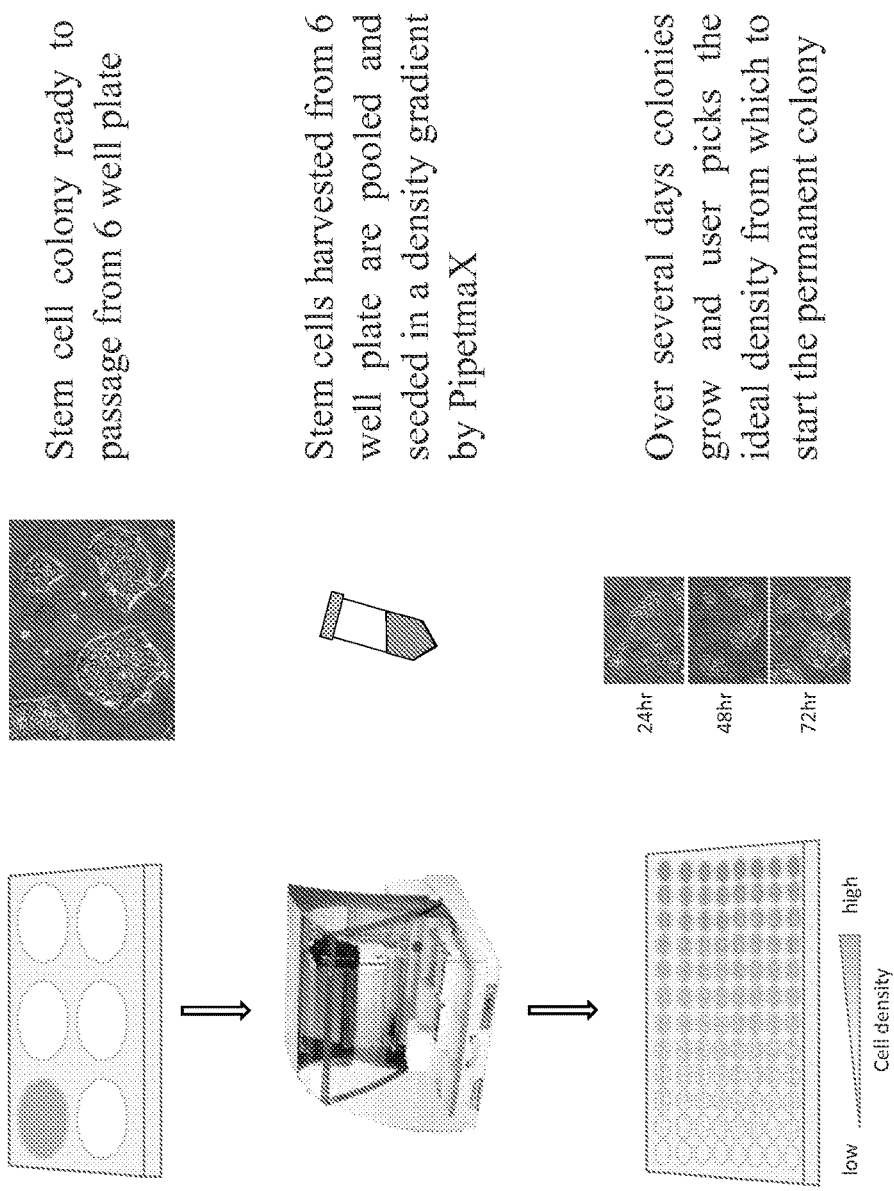
FIGS. 6-17 show diagrammatic overviews of various automated stem cell handling procedures in accordance with various embodiments.
Figure 7:
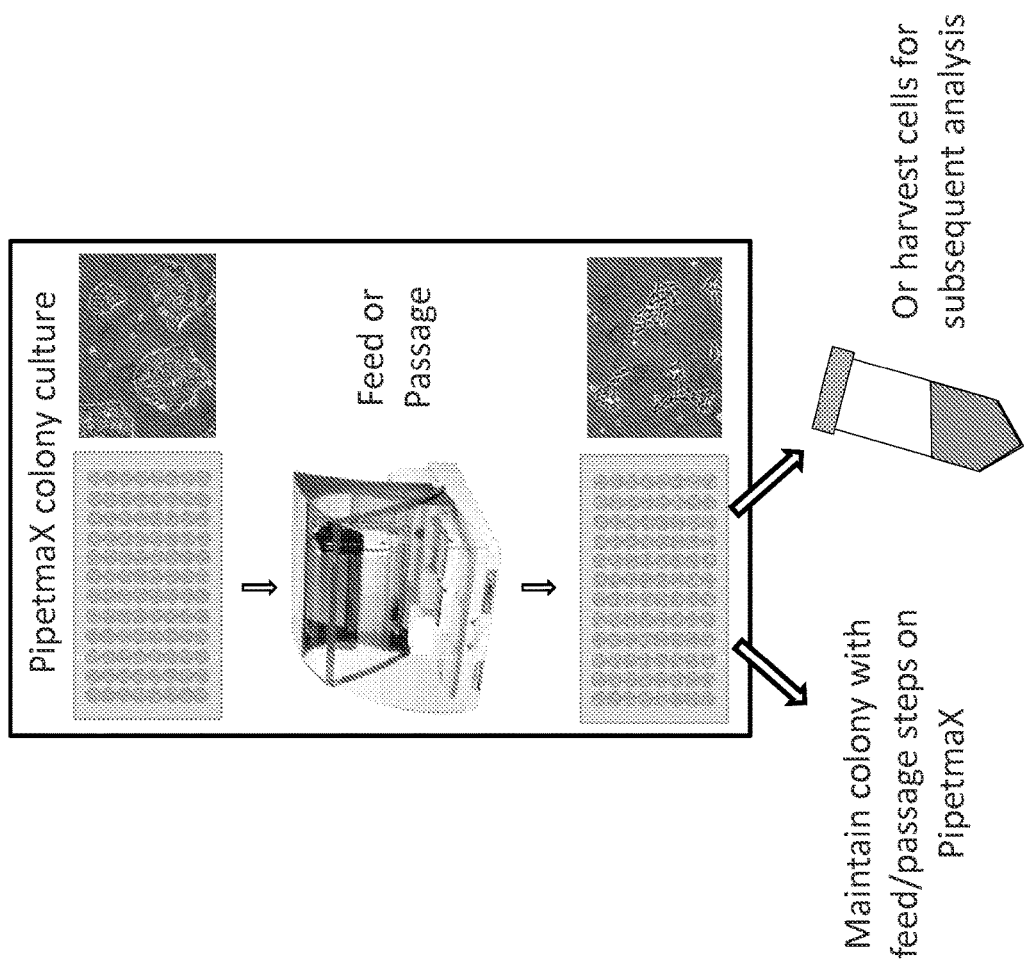
Figure 8:
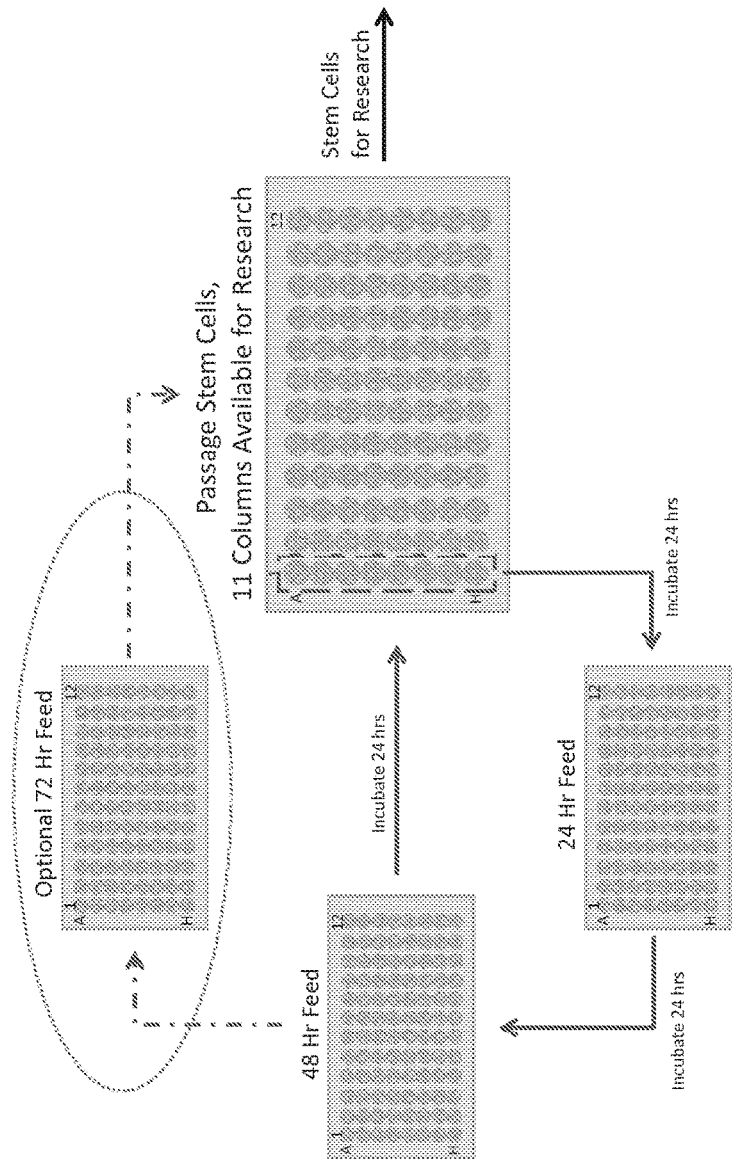
Figure 9:
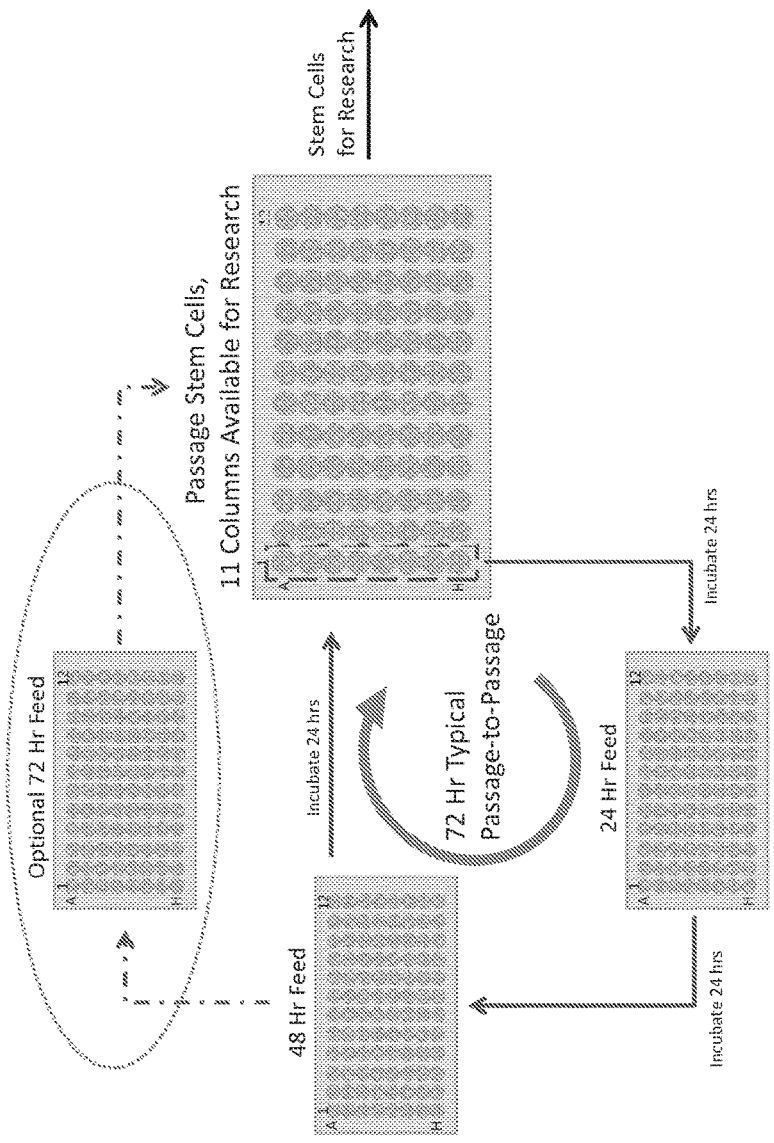
Figure 10:
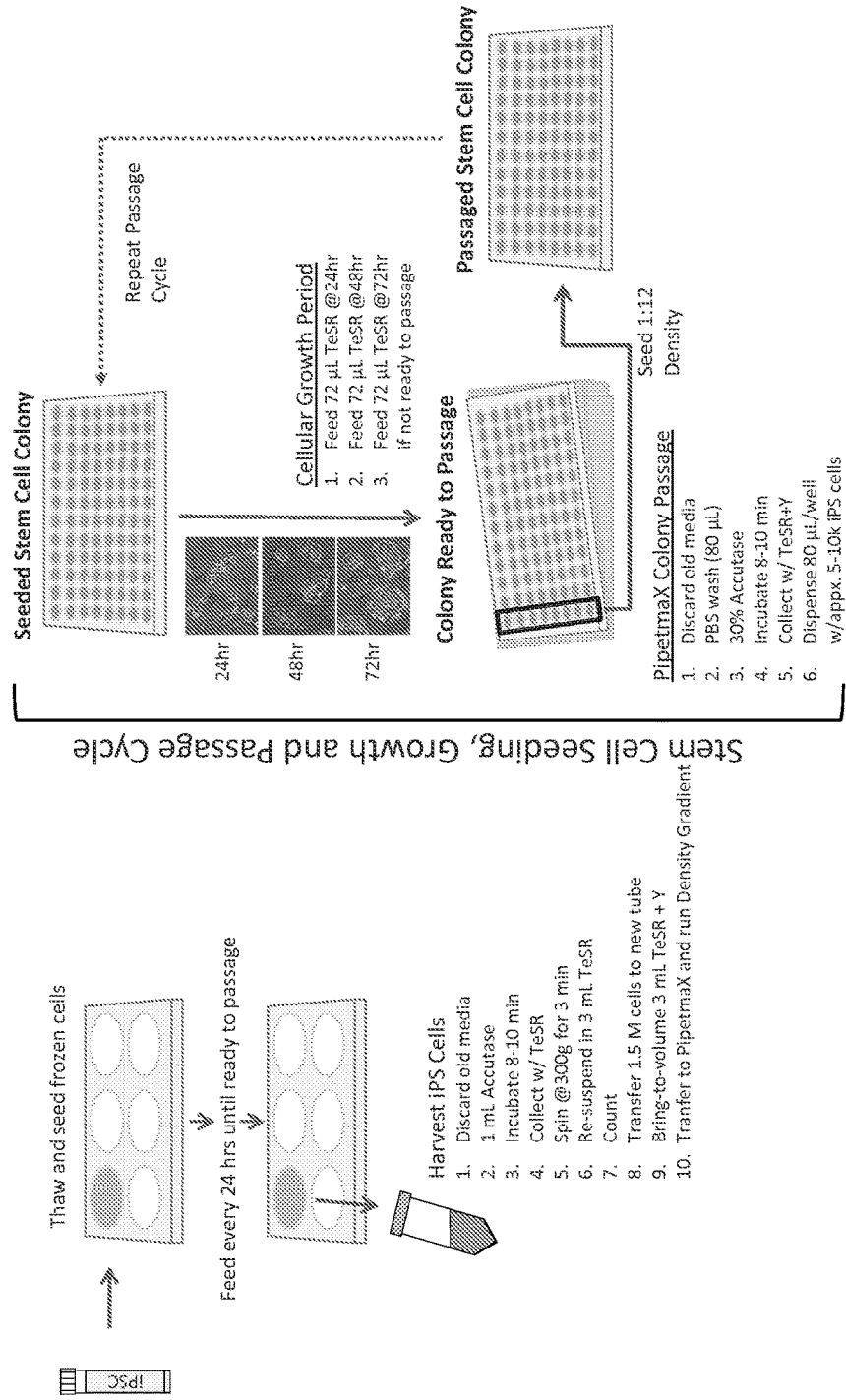
Figure 11:
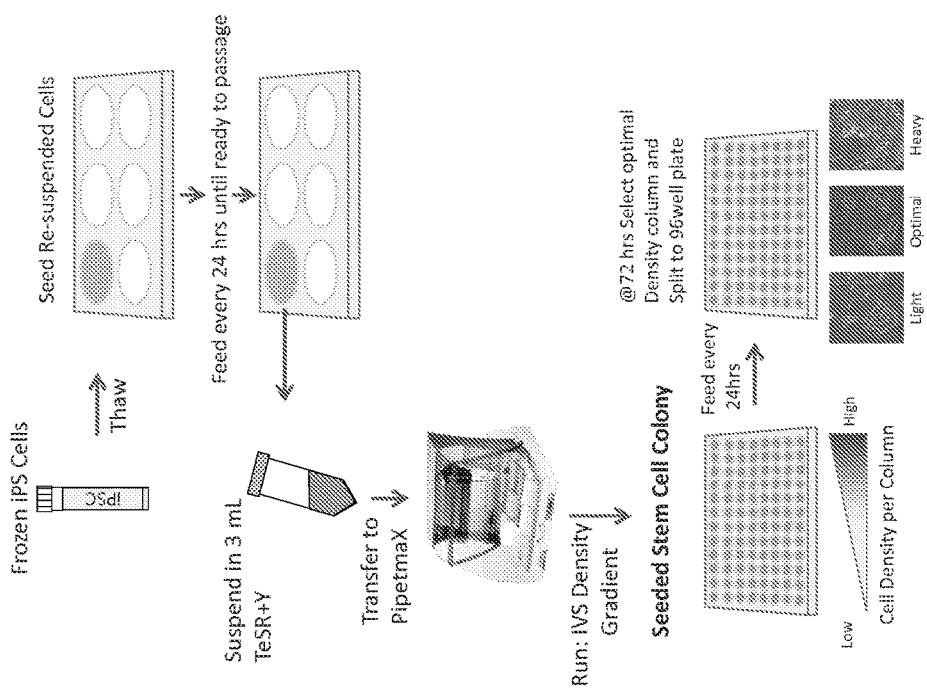
Figure 12:
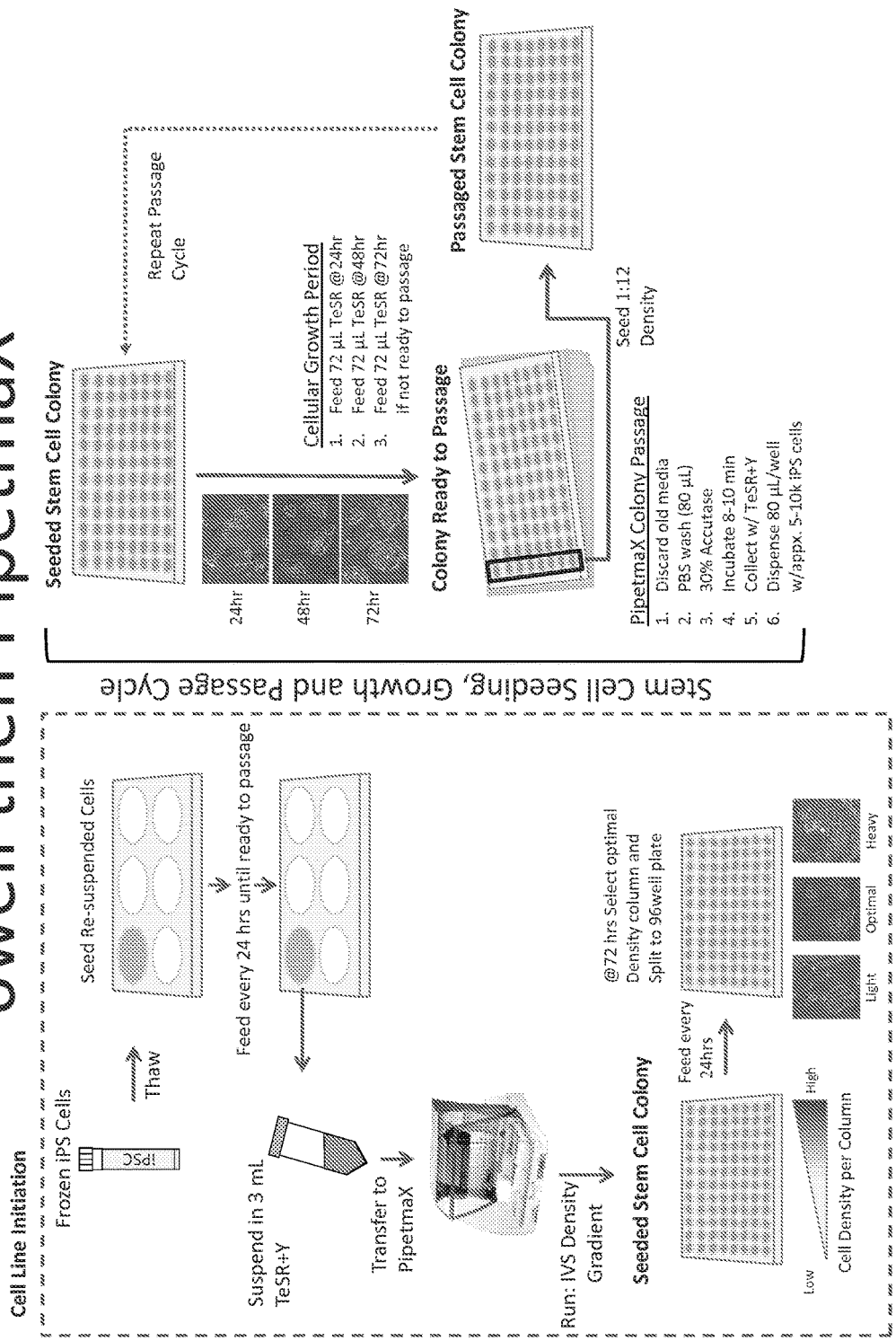
Figure 13:
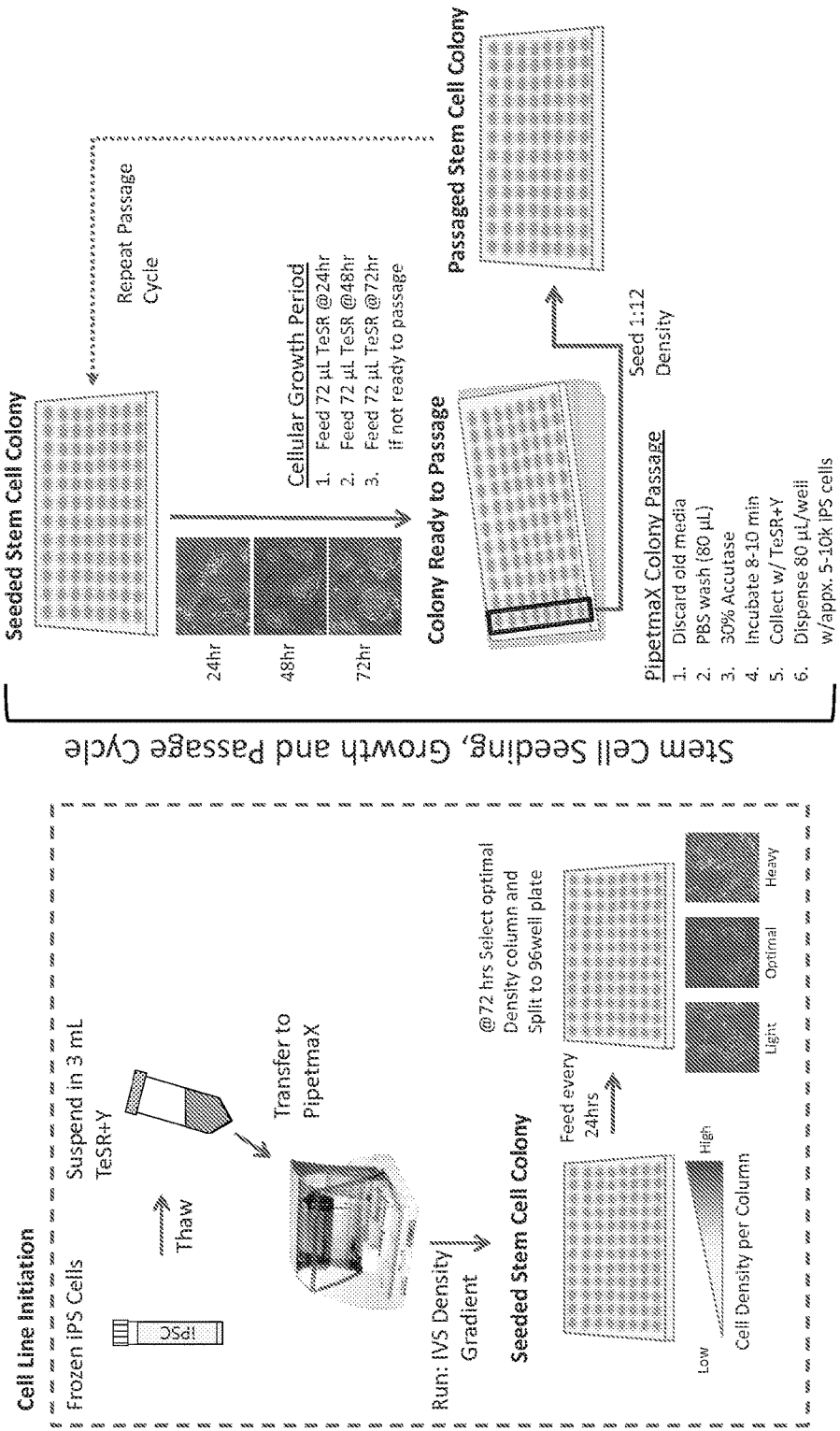
Figure 14:
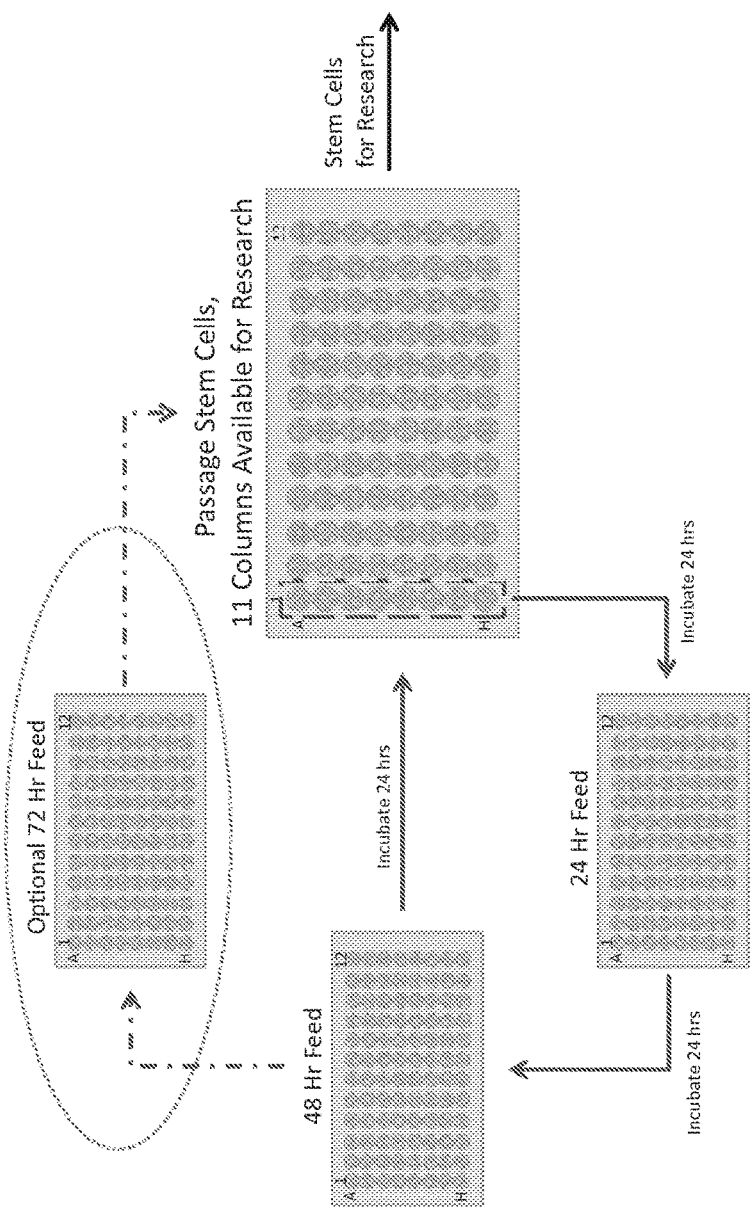
Figure 15:
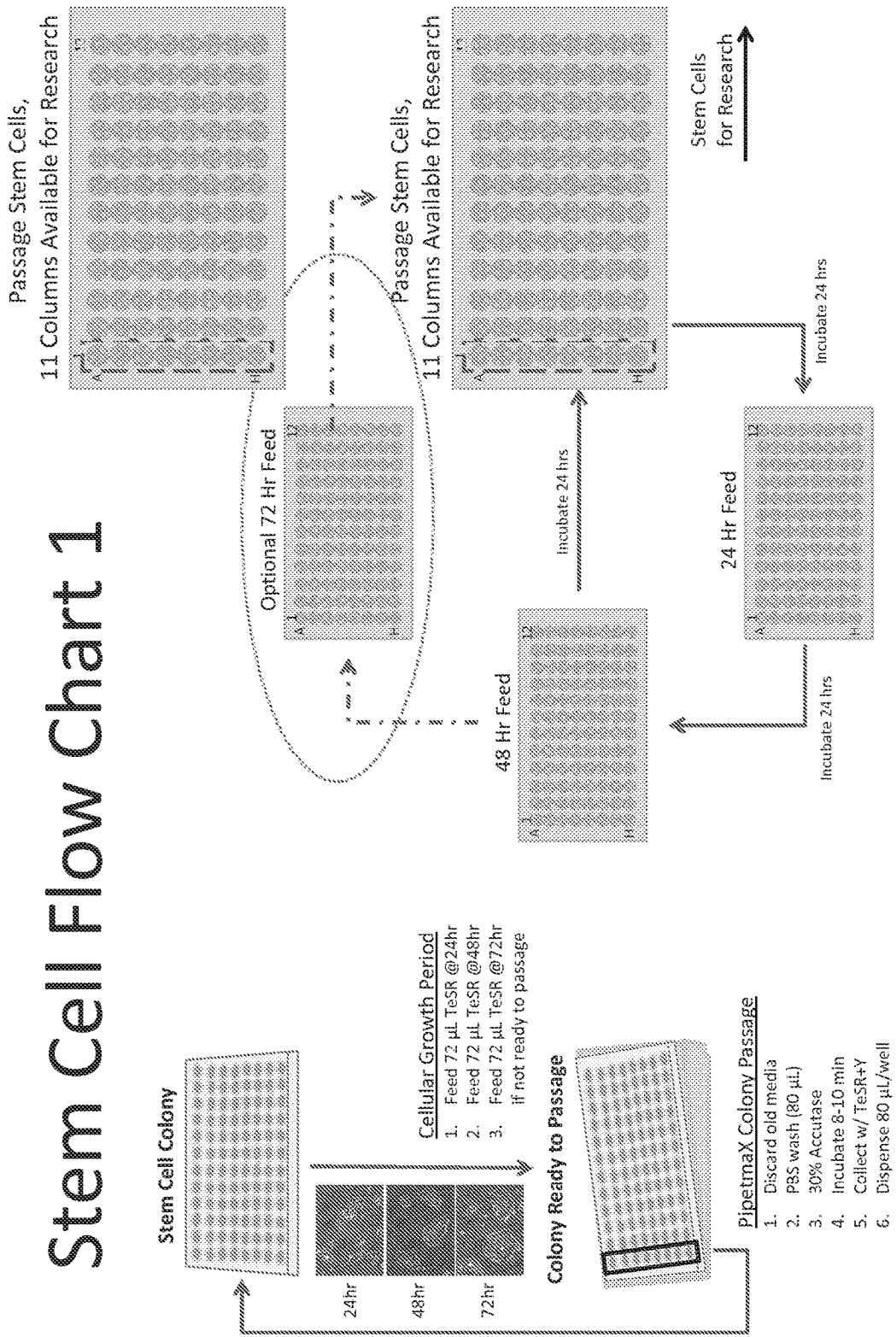
Figure 16:
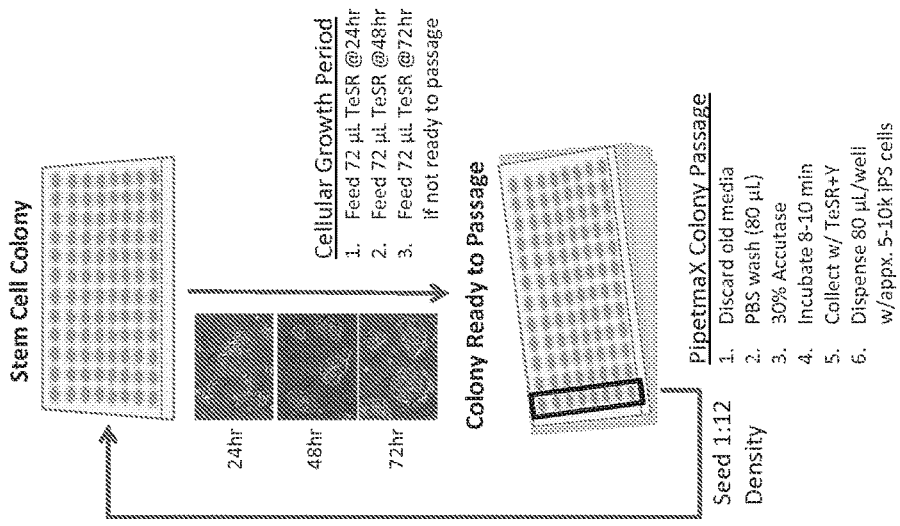
Figure 17:
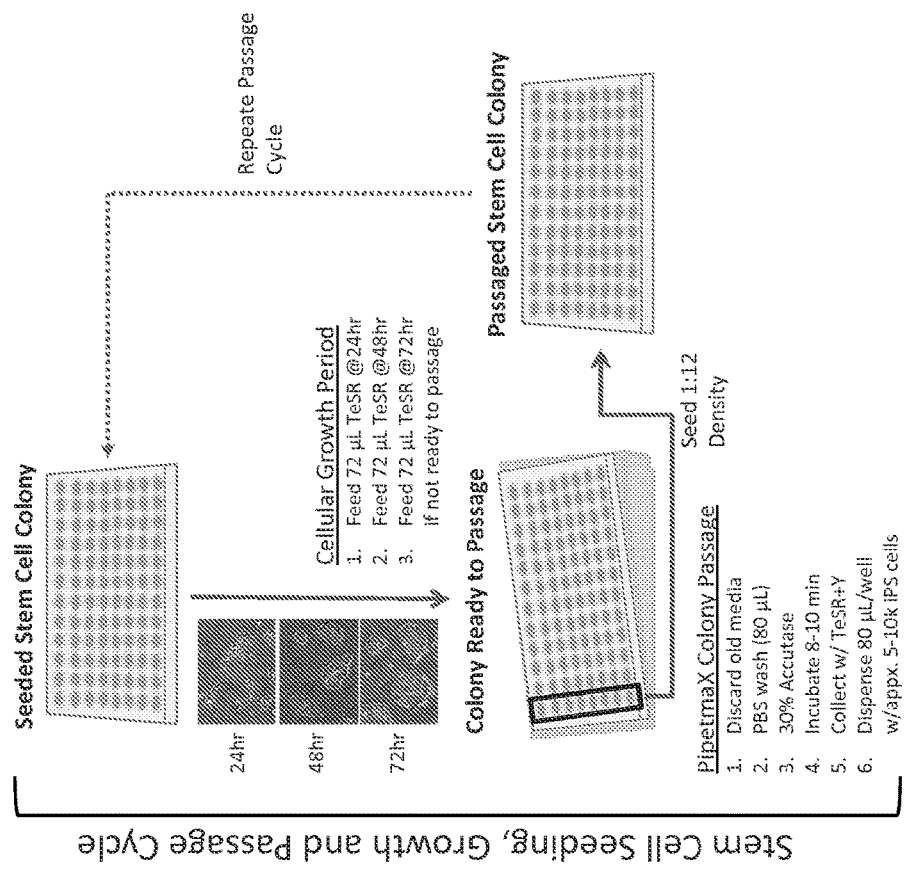

As an initial step towards demonstrating how the disclosed automated stem cell expansion methods and systems may be used to identify and optimize culture conditions that are best suited for pluripotent stem cells, the above-mentioned iPSCs were cultured in different culture media (see FIG. 4, panels A-B). Stem cells grown in a commercially-available media, E8 (FIG. 4, panel B, Life Technologies), which was developed by screening different cell culture conditions, showed different morphology than stem cells cultured using a different commercially-available media, mTeSR1 (FIG. 4, panel A, Stem Cell Technologies, Inc.). Both E8 and mTeSR1 culture media have been shown to maintain pluripotency when used with various human pluripotent stem cell lines. However, induced pluripotent stem cell lines (iPSCs) maintained in E8 did not differentiate into CMs with high efficiency (where high efficiency is in the range of about 80%-90% of pluripotent stem cells differentiate into CMs) using the small molecule protocol (see Lian et al. referenced herein). In addition to maintaining pluripotency, the ability of iPSCs to differentiate into desired cell types using specific protocols favors use of iPSCs to mass-produce desired cell types for various applications.

The rate of stem cell expansion is a factor in scale-up production of iPSCs. It has been preliminary observed that a size distribution of colonies at seeding affects pluripotency and the subsequent proliferation rate of the stem cells, in particular that small and uniform starting colony size increases the rate of iPSC proliferation. It was also found that the duration and concentration of enzyme (e.g. Accutase®) treatments to break up colonies led to varied colony sizes at seeding.

The time to reach to the critical colony size to passage was monitored and recorded. These time periods are generally monitored for ten passages because pluripotent stem cells need time to adopt new passage conditions. The smallest "colony" size should be single cells, and it is expected that the single cell passage achieves the most rapid proliferation. Once it has been determined what the best passage conditions are to achieve the fastest proliferation without visual abnormality of colonies, the pluripotent tests are conducted to confirm pluripotency maintenance and cardiac differentiation using the small molecules. Alternatively, the rate of proliferation can be measured by fixing colony passage period for all conditions to 72 hours, and viability of cells can be measured using viability assay kits, such as CCK8 (from Dojindo, which involves analyzing colorimetric changes of media due to activities of cellular dehyrogenase, directly proportional to the number of living cells). The size distribution of colonies can be an important factor which influences the iPSC proliferation rate; colonies can be pre-treated with Cell Strainer (BD Biosciences), e.g. with 40, 70, 100 µm or other suitable pore sizes, to control the size distribution of the colonies. The Cell Strainer homogenizes the colony size distribution, and it is expected that iPSCs with small and uniform colony size proliferate faster than larger colony sizes.

iPSCs cultured using various formulations of media showed similar morphology, including iPSC colonies cultured with the commercially-available mTeSR1 media (see FIG. 4, panels A (mTeSR1) and B (E8 media)). In various embodiments, custom culture media can be developed and tested in order to optimize growth while maintaining pluripotency. To demonstrate an effective use of the disclosed systems and methods in optimizing cell culture conditions, the efficiency of any custom-made media will be analyzed for pluripotent (e.g. iPSC) stem cell cultures. By varying concentrations of different key supplements in the media, pluripotency test analyses of iPSC expansion rates will be performed as described above. A typical test can be conducted as follows. To test the effects of growth factors on pluripotency and proliferation, the concentration of the growth factor will be varied using a robotic liquid handling system (e.g. PipetmaX™, for example at concentrations 0, 0.1, 0.3, 1, 3, 10, 30 nM) and morphology of colonies and expression of pluripotent surface marker (SEE4) will be analyzed in live cells using fluorescently-conjugated antibodies. Once conditions have been identified to satisfy the pluripotency and high proliferation rate, further pluripotency tests will be performed using other assays. It is expected that these studies will show the effectiveness of the disclosed methods and systems, which utilize robotic liquid handling systems, to identify new and cost-effective media to maintain pluripotent stem cells.

The disclosed automated stem cell culture methods and systems can be used with a number of pluripotent stem cell lines. Embodiments of the disclosed methods and systems will be implemented using various iPSC lines that were reprogrammed from patients with genetic disorders as well as genetically engineered iPSC lines that express, for example, gene expression markers and knocked-down protein expression. Candidate cell lines include iPSCs derived from Duchenne muscular dystrophy (DMD) and amyotrophic lateral sclerosis patients (both of which are available from System Biosciences) and iPSCs expressing green fluorescent protein (GFP) under a cardiac-specific troponin T promoter. The validation data will report 1) ability to maintain pluripotency, 2) iPSC expansion rates, and/or 3) ability to differentiate into cardiomyocytes using small molecule protocol.

EXAMPLES

The following non-limiting Examples are intended to be purely illustrative, and show specific experiments that were carried out in accordance with embodiments of the invention.

Example 1

The following example describes procedures for culturing stem cells according to embodiments of the invention:
1.0 Materials
1.1 Sterile square 96 well plate with dual inserts [Ibidi 89621, IVS Dual Inserts]
1.2 (1) Sterile 4 deepwell reservoir [Seahorse 201308-100]
1.3 Pre-treatment—DMEM, 10% FBS
1.4 Tissue solution [Follow IVS Tissue Fabrication Protocol (see Lam et al. 2011, Marquez et al. 2009, Genin et al. 2011, and Asnes et al. 2006, each of which is incorporated herein by reference in its entirety)]
1.5 Supplemental media—DMEM, 3% FBS, 2.50×PSG
1.6 PIPETMAN Filter Tips D200
2.0 Procedure
2.1 Pretreatment
2.1.1 Remove 96 well plate with dual inserts from packaging and place on PIPETMAX in position 4
2.1.2 Place sterile reservoir in position 6 on PIPETMAX stage
2.1.3 Add 25 mL pre-treatment solution to well 1 of reservoir in position 6 [4 C-24 C]
2.1.4 Run program 1 to aliquot 200 µl pre-treatment per well
2.1.5 Cover 96 well and leave on PIPETMAX for tissue solution prep.
2.2 Make tissue solution following IVS Tissue Fabrication Protocol—set on ice
2.3 Remove pre-treatment solution
2.3.1 Remove cover from 96 well
2.3.2 Run program 2 to remove pre-treatment from well [Discarded pretreatment in well 4 of reservoir in position 6]
2.3.3 Use a vacuum with sterile Pasteur pipette to remove remaining pre-treatment solution
2.4 Aliquot Tissue Solution
2.4.1 Open sterile reservoir, found in −20 C, and place in position 5 on PIPETMAX
2.4.2 Retrieve tissue solution in 50 ml conical on ice
2.4.3 Triturate 4× to mix using cold 10 mL serological
2.4.4 Transfer 29 mL tissue solution to cold reservoir, well 1 [Tissue solution should remain 4 C-10 C if possible]
2.4.5 Triturate 2× in trough before discarding serological
2.4.6 Run program 3 to aliquot 270 µl Tissue solution per well
2.4.7 Cover 96 well
2.5 Incubate 96 well in 37 C incubator, 5% CO2, for 60-90 minutes
2.6 Add Supplemental Media
2.6.1 Add 25 mL pre-warmed supplemental media to well 1 of reservoir in position 6 [−37 C]
2.6.2 Remove 96 well from incubator and place on PIPETMAX in position 4

2.6.3 Run program 4 to bring volume up to 440 ul per well, dispense 170 ul per well 2.6.4 Cover and return 96 well to 37 C 5% CO2 incubator for minimum 24 hours Program 1 (Pre-Treatment)
Tips should touch off if Program 2 only takes off a percentage of the pretreatment solution
Treatment can be added to the center of the well
Temperature is not a factor, 4 C-37 C is acceptable, room temp is normally used
Dispense speed can be quick
Program 2 (Pre-Treatment Removal)
Remove fluid from wells
Program 3 (Tissue Solution Aliquot)
optional cell mixing
maintain temperature, this temperature can be 4-10 C but should not fluctuate
Dispense speed should be average
Current mixing protocol:
load tips
mix tissue solution in reservoir (150 µl twice)
aspirate 140 µl
dispense in 96 well row 1
Perform a tip touch to liquid to ensure droplets do not remain on tip.
mix tissue solution in reservoir (150 µl twice)
aspirate 140 µl
dispense in 96 well row 1
Use a Bio1000 mix to mix tissue solution in 96 well, 100 ul once
repeat mixing and dispensing for entire 96 well plate eject tips
optional mixing protocol
load tips
aspirate 140 µl Tissue solution in reservoir
dispense in 96 well row 1
Perform a tip touch to liquid to ensure droplets do not remain on tip.
aspirate 140 µl Tissue solution in reservoir
dispense in 96 well row 1
Perform a tip touch to liquid to ensure droplets do not remain on tip.
repeat dispensing for entire 96 well plate
eject tips
Program 4 (Supplemental Media)
media should be warm to not shock the cells~37 C but can range from 30-37 C
dispense speed should be slow, drop-wise to not pierce jelly-like polymerizing tissue
Tip touch off could be used if the tip does not touch the polymerized tissue solution.

Example 2

Referring now to FIGS. 5A-5F, in which steps to the method in accordance with the present invention has been described. The following describes routines carried out by an application software program operating in conjunction with the robotic liquid handling system to seed stem cells (ASC 1.1), feed colonies (ASC 1.2), passage colonies (ASC 1.3), and harvesting colonies (ASC 1.4).

ASC1.1—Density Gradient Stem Cell Seeding
S1.
Media on plate keeps Matrigel coating from drying out
Tips are positioned in corner of well to remove maximal media to keep seeded stem cell media as close to 1× as possible
robot removes 2 columns at a time before discarding thus significantly reducing operating time
S2.
Robot dispenses different amounts of mTeSR1+Y27632 to each column based on cell seeding volumes to accomplish proper dilution yet end up with same final volume across plate.
Tip height is low enough so 20 µl dispense droplet volume will touch bottom of well and get drawn onto the bottom rather than hung up on side of well wall thus preventing well from drying out which completely disrupts stem cell seating.
S3.
Mix cells using aspiration and dispense by 8 tips in trough containing cells in suspension
Cells settle and will collect at the bottom of the trough relatively quickly (5-10 minutes)
Homogeneous mixture is required to produce accurate cell density gradient
S4.
Cell mixture is at 1.0× concentration
Columns 12 and 11 are seeded in decreasing volumes respectively to create the two highest density columns
S5.
Tips are only accurate 20-200 µL; to achieve wide range of cell densities dilutions are needed
Fresh mTeSR1+Y27632 is added to cell solution (Cells+mTeSR1+Y27632) to reduce concentration to 0.5×
Cells are mixed using aspiration and dispense, 3×, to ensure homogeneous solution
S6.
Cell mixture is at 0.5× concentration
columns 6 through 10 are seeded in decreasing volumes respectively to create medium-high density columns
S7.
Tips are only accurate 20-200 µL, to achieve wide range of cell densities dilutions are needed.
Fresh mTeSR1+Y27632 is added to cell solution (Cells+mTeSR1+Y27632) to reduce concentration to 0.25×
Cells are mixed using aspiration and dispense, 3×, to ensure homogeneous solution
S8.
Cell mixture is at 0.25× concentration
columns 3 through 5 are seeded in decreasing volumes respectively to create medium-low density columns
S9.
Tips are only accurate 20-200 µL, to achieve wide range of cell densities dilutions are needed.
Fresh mTeSR1+Y27632 is added to cell solution (Cells+mTeSR1+Y27632) to reduce concentration 0.0625×
Cells are mixed using aspiration and dispense, 3×, to ensure homogeneous solution
S10.
Cell mixture is at 0.0625× concentration
columns 1 and 2 are seeded in decreasing volumes respectively to create low density columns
S11.
Plate are covered and labeled for subsequent cell culture
ASC1.2
S101
Plate sits on tilt rack, needed so vertical tapered pipettes can reach corners of well to remove maximum amount of media volume. Also helps dead cells accumulate in corner.
Maximum removal needed to: 1) New media may be negatively affected by residual media either by dilution or component action (e.g. growth factors) 2) remove maximum number of dead cells which may otherwise negatively affect live cells 4) remove cell excreted waste 4) replenish nutrients needed Robot aspirates more volume than actual liquid in well to control higher evaporation rates along outer wells. This keeps inside vs. outside wells at the same media concentration immediately post feed

S102 mTeSR1 aliquoted to feed along inside wall of tilted plate to: 1) prevent disruption to cell layer 2) create bubble free media when finished 3) help reduce "sputtering" of media from tips when close to fully discharged 72 μl mTeSR1 found to sustain stem cells without differentiation. This values aims to minimize media volume required to maintain cells in a desirable state while also minimizing cost.

ASC1.3

S201

Plate sits on tilt rack, needed so vertical tapered pipettes can reach corners of well to remove maximum amount of media volume. Also helps dead cells accumulate in corner.

Maximum removal needed to: 1) New media may be negatively affected by residual media either by dilution or component action (e.g. growth factors) 2) remove maximum number of dead cells which may otherwise negatively affect live cells 4) remove cell excreted waste 4) replenish nutrients needed Robot aspirates more volume than actual liquid in well to control higher evaporation rates along outer wells. This keeps inside vs. outside wells at the same media concentration immediately post feed

S202

PBS wash to further reduce disassociation inhibitors and dead cells

PBS volume is higher than media feed volume for complete well wash

S203

Disassociation reagent, Accutase, added to column being passaged

Accutase volume and concentration was found to be optimal at 25 μL, and 30% respectively to cover well bottom and dissociate cells A minimal amount of total Accutase is critical to successful robotic splitting. It must provide adequate cell dissociation but not require the operator to centrifuge the cells which would add significant operator time and effort.

Too much Accutase in the seeding mix results in cells failing to adhere to well bottoms.

S204

Media on plate keeps Matrigel coating from drying out

Tips are positioned in corner of well to remove maximal media to keep seeded stem cell media as close to 1× as possible robot removes 2 columns at a time before discarding Performed while disassociation reagent takes effect

S205

Matrigel coating is compromised if it dries out

Minimal volume to keep well bottom surface wet is added, 20 μL

S206

Large volume of mTeSR1+Y27632 is transferred and dispensed at high flow rate near top of well to flush cells down to collection location Volume is then aspirated from collection location and another high flow rate flush is performed near the top of the well This action helps to agitate cells from surface and to break up colonies into more uniform clumps which is important for even seeding in the new plate Entire volume of cell solution is aspirated and transferred to mTeSR1+Y27632 reservoir to create cell solution

S207

Uniform colony densities across all 96 wells of passaged colony plate are expected, homogeneous solution is required since cells pellet on the bottom over time Perform bed movement to slosh & swirl cells Perform aspiration from bottom and dispense from offset near-bottom to induce swirl mixing

S208

Cell solution is mixed before each aspiration, then two columns are seeded before repeating Mixing is performed to ensure homogeneous cell solution to create uniform plate density S209 Plate is labeled for subsequent cell culture processes

ASC1.4

S301

Plate sits on tilt rack, needed so vertical tapered pipettes can reach corners of well to remove maximum amount of media volume. Also helps dead cells accumulate in corner.

Maximum removal needed to: 1) New media may be negatively affected by residual media either by dilution or component action (e.g. growth factors) 2) remove maximum number of dead cells which may otherwise negatively affect live cells 4) remove cell excreted waste 4) replenish nutrients needed All wells aspirated

S302

PBS wash of entire plate

PBS wash to further reduce disassociation inhibitors and dead cells

PBS volume is higher than media feed volume for complete well wash

S303

Disassociation reagent, Accutase, added to all columns

Minimal amount of Accutase used (see S203 steps A,B,C above for explanation)

S304

Large volume of mTeSR1 is transferred and dispensed at high flow rate near top of well to flush cells down to collection location Volume is then aspirated from collection location and another high flow rate flush is performed near the top of the well Entire volume of cell solution is aspirated and transferred to mTeSR1 reservoir to create cell solution This step continues until all columns are harvested

S305

A technician manually pipettes the cell solution from their reservoir and dispenses into a collection tube Cells can be spun down and re-suspended as need for subsequent analysis All publications, patents and patent applications referenced in this specification are indicative of the level of ordinary skill in the art to which this application pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

REFERENCES

1. Chen, G., D. R. Gulbranson, et al. (2011). "Chemically defined conditions for human iPSC derivation and culture." Nature methods 8(5): 424-429.
2. Ebert, A. D., P. Liang, et al. (2012). "Induced Pluripotent Stem Cells as a Disease Modeling and Drug Screening Platform." Journal of Cardiovascular Pharmacology 60(4): 408-416 410.1097/FJC.1090b1013e318247f318642.
3. Ferreira, L. M. R. and M. A. Mostajo-Radji (2013). "How induced pluripotent stem cells are redefining personalized medicine." Gene 520(1): 1-6.
4. Haraguchi, Y., K. Matsuura, et al. (2013). "Simple suspension culture system of human iPS cells maintaining their pluripotency for cardiac cell sheet engineering." Journal of Tissue Engineering and Regenerative Medicine.
5. Hazeltine, L. B., C. S. Simmons, et al. (2012). "Effects of substrate mechanics on contractility of cardiomyocytes generated from human pluripotent stem cells." International journal of cell biology 2012: 508294.
6. Jung, S., K. M. Panchalingam, et al. (2012). "Large-scale production of human mesenchymal stem cells for clinical applications." Biotechnology and applied biochemistry 59(2): 106-120.
7. Kehoe, D. E., D. Jing, et al. (2010). "Scalable stirred-suspension bioreactor culture of human pluripotent stem cells." Tissue engineering. Part A 16(2): 405-421.
8. Lian, X., C. Hsiao, et al. (2012). "Robust cardiomyocyte differentiation from human pluripotent stem cells via temporal modulation of canonical Wnt signaling." Proceedings of the National Academy of Sciences of the United States of America 109(27): E1848-1857.
9. Lian, X., J. Zhang, et al. (2013). "Directed cardiomyocyte differentiation from human pluripotent stem cells by modulating Wnt/beta-catenin signaling under fully defined conditions." Nature protocols 8(1): 162-175.
10. Lotz, S., S. Goderie, et al. (2013). "Sustained levels of FGF2 maintain undifferentiated stem cell cultures with biweekly feeding." PLoS One 8(2): e56289.
11. Muller, F. J., B. M. Schuldt, et al. (2011). "A bioinformatic assay for pluripotency in human cells." Nature methods 8(4): 315-317.
12. Outten, J. T., X. Cheng, et al. (2011). "A high-throughput multiplexed screening assay for optimizing serum-free differentiation protocols of human embryonic stem cells." Stem Cell Research 6(2): 129-142.
13. Syed, B. A. and J. B. Evans (2013). "Stem cell therapy market." Nature reviews. Drug discovery 12(3): 185-186.
14. Takahashi, K. and S. Yamanaka (2006). "Induction of pluripotent stem cells from mouse embryonic and adult fibroblast cultures by defined factors." Cell 126(4): 663-676.
15. Walker, J. (2010). "Disease in a dish: a new approach to drug discovery." Regenerative medicine 5(4): 505-507.
16. Wetterstrand, K. A. "DNA Sequencing Costs: Data from the NHGRI Genome Sequencing Program (GSP) Available at: www.genome.gov/sequencingcosts."
17. Ludwig, T. E., et al., Feeder-independent culture of human embryonic stem cells. Nat Meth, 2006. 3(8): p. 637-646.
18. Lam, V. and T. Wakatsuki, Hydrogel Tissue Construct-Based High-Content Compound Screening. Journal of Biomolecular Screening, 2011. 16(1): p. 120-128.
19. Marquez, J. P., et al., High-Throughput Measurements of Hydrogel Tissue Construct Mechanics. Tissue Eng Part C Methods, 2009.
20. Genin, G., et al., eds. Cell-Cell Interactions and the Mechanics of Cells and Tissues Observed in Bioartificial Tissue Constructs., ed. A. H. Wagoner Johnson, Brendan A. C. 2011, Springer.
21. Asnes, C. F., et al., Reconstitution of the Frank-Starling mechanism in engineered heart tissues. Biophys J, 2006. 91(5): p. 1800-10.

What is claimed is:

1. An automated method for culturing stem cells using a robotic liquid handling system including a translatable bed and a movable multi-channel pipette, the method comprising the steps of:
    placing a suspension of stem cells in a first trough of the multi-trough plate positioned on the bed;
    placing a cell culture media in a second trough of the multiple-trough plate;
    mixing the suspension of stem cells in the multi-trough plate by linearly moving the translatable bed back and forth;
    plating stem cells in a first multi-well cell culture plate located on the bed such that at least two wells of the first multi-well cell culture plate have different densities of stem cells by
        using the multi-channel pipette, transferring different volumes of the suspension of stem cells from the first trough to the at least two wells of the first multi-well cell culture plate, and
        using the multi-channel pipette, transferring different volumes of the cell culture media from the second trough to the at least two wells of the first multi-well cell culture plate,
        wherein the different volumes of the suspension of stem cells and the different volumes of cell culture media are defined to achieve the different densities of stem cells in the at least two wells of the first multi-well cell culture plate, and
        wherein the back and forth linear motion of the translatable bed maintains the suspension of stem cells in the first trough at a uniform concentration during the plating;
    selecting a well of the first multi-well cell culture plate having a desired density of stem cells after growth of cell colonies in the first multi-well cell culture plate;
    using the multi-channel pipette, transferring the cells of the selected well of the first multi-well cell culture plate to a plurality of wells of a second multi-well cell culture plate, wherein the first multi-well cell culture plate is positioned on a heated, angled adapter located on the bed while the cells are transferred from the selected well of the first multi-well cell culture plate to the plurality of wells of the second multi-well cell culture plate;
    using the multi-channel pipette, transferring a portion of the cell culture media to the plurality of wells of the second multi-well cell culture plate; and
    feeding the stem cells in the plurality of wells of the second multi-well cell culture plate, by removing the cell culture media from the plurality of wells of the second multi-well cell culture plate and adding new cell culture media to the plurality of wells of the second multi-well cell culture plate.

2. The method of claim 1, wherein transferring the cells of the selected well to a plurality of wells of the second multi-well cell culture plate comprises detaching the stem cells from the first multi-well cell culture plate using one of an enzymatic method or a chemical method.

3. The method of claim 2, wherein transferring the cells of the selected well to a plurality of wells of the second multi-well cell culture plate further comprises guiding the multi-channel pipette such that a plurality of pipette tips of the multi-channel pipette are adjacent side walls of a plurality of the wells of the second multi-well cell culture plate.

4. The method of claim 3, wherein guiding the multi-channel pipette comprises guiding the multi-channel pipette with an accuracy of at least one micrometer.

5. The method of claim 1, wherein the heated, angled adapter is angled at an angle of approximately 10°.

6. The method of claim 1, further comprising determining a density of stem cells in at least one well of the second multi-well cell culture plate and splitting the stem cells of the at least one well of the second multi-well cell culture plate if the density is greater than a predetermined level.

7. The method of claim 6, wherein determining a density of stem cells in at least one well of the second multi-well cell culture plate comprises comparing the stem cells in at least one well of the second multi-well cell culture plate with a plurality of images of cultured stem cells to determine a density.

8. The method of claim 1, wherein removing cell culture media from the plurality of wells of the second multi-well cell culture plate comprises guiding the multi-channel pipette such that a plurality of pipette tips of the multi-channel pipette are located at or near a lowest point of the plurality of the wells of the second multi-well cell culture plate.

9. The method of claim 1, wherein the multi-well plate is one of a 24-well plate, a 48-well plate, and a 96-well plate.

10. The method of claim 1, wherein the wells of the first and second multi-well cell culture plate are coated with extracellular matrix material.

11. The method of claim 1, wherein the stem cells are pluripotent stem cells.

12. The method of claim 11, further comprising testing the stem cells of the second multi-well cell culture plate for pluripotency.

13. The method of claim 1, wherein each of the wells of the second multi-well cell culture plate has a bottom surface area of between 0.3 and 0.4 square centimeters.

14. The method of claim 1, wherein a bottom of each of the wells of the second multi-well cell culture plate has a ratio of circumference to area of between 0.56 and 0.64.

15. The method of claim 1, further comprising adding at least one of a compound and a gene to at least one of the wells of the second multi-well cell culture plate to induce differentiation.

16. The method of claim 15, wherein the at least one of a compound and a gene induces differentiation of the stem cells into cardiac myocytes.

17. The method of claim 1, further comprising:

positioning the first multi-well cell culture plate on the heated, angled adapter; and treating the stem cells in the selected well of the first multi-well cell culture plate with an enzyme to promote cell detachment from the surface of the selected well, wherein the heated, angled adapter is configured to maintain the first multi-well cell culture plate at an elevated temperature while stem cells in the selected well are treated with the enzyme.

18. The method of claim 1, wherein plating the stem cells in the first multi-well cell culture plate located on the bed further includes controllably dispensing different volumes of stem cells in wells of each column of the first multi-well cell culture plate to create a density gradient by transferring a first volume of the suspension of stem cells from the first trough into at least one well in a first column of the first multi-well cell culture plate; and transferring a second volume of the suspension of stem cells from the first trough into at least one well in a second column of the first multi-well cell culture plate, wherein the first volume of the suspension of stem cells is different from the second volume of the suspension of stem cells.

19. The method of claim 18, wherein selecting the well of the first multi-well cell culture plate having the desired density of stem cells includes identifying a well of the first multi-well cell culture plate with a density of stem cells determined to promote differentiation of pluripotent stem cells into a particular cell or tissue type.

* * * * *